(12) United States Patent
Furukawa

(10) Patent No.: US 9,374,388 B2
(45) Date of Patent: Jun. 21, 2016

(54) POLICY ARBITRATION METHOD, POLICY ARBITRATION SERVER, AND PROGRAM

(75) Inventor: Ryo Furukawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 27 days.

(21) Appl. No.: 14/002,624

(22) PCT Filed: Mar. 2, 2012

(86) PCT No.: PCT/JP2012/055459
§ 371 (c)(1),
(2), (4) Date: Aug. 30, 2013

(87) PCT Pub. No.: WO2012/118205
PCT Pub. Date: Sep. 7, 2012

(65) Prior Publication Data
US 2013/0340036 A1   Dec. 19, 2013

(30) Foreign Application Priority Data
Mar. 3, 2011   (JP) ................................. 2011-045911

(51) Int. Cl.
*G06F 21/00*   (2013.01)
*H04L 29/06*   (2006.01)
(Continued)

(52) U.S. Cl.
CPC ............ *H04L 63/20* (2013.01); *G06F 21/6245* (2013.01); *G06F 19/322* (2013.01); *G06F 21/604* (2013.01); *H04L 63/102* (2013.01)

(58) Field of Classification Search
CPC ........................................................ H04L 63/20
USPC ................................................................. 726/1
See application file for complete search history.

(56) References Cited

U.S. PATENT DOCUMENTS

2002/0104015 A1   8/2002   Barzilai et al.
2003/0088520 A1*  5/2003   Bohrer et al. .................. 705/74
(Continued)

FOREIGN PATENT DOCUMENTS

CN   102314449 A   1/2012
JP   05-250415 A   9/1993
(Continued)

OTHER PUBLICATIONS

"Platform for Privacy Preferences (P3P) Project; Enabling smarter Privacy Tools for the Web", PLING—W3C Policy Languages Interest Group, P3P: The Platform for Privacy Preferences, Oct. 3, 2007, [online], [searched on Feb. 23, 2011], the Internet <URL: http://www.w3.org/P3P/>.

(Continued)

*Primary Examiner* — Jeffrey Pwu
*Assistant Examiner* — William Corum, Jr.
(74) *Attorney, Agent, or Firm* — Sughrue Mion, PLLC

(57) ABSTRACT

A policy arbitration method comprises: entering a user policy in which a privacy information holder describes at least one rule that is a pair of a data type of privacy information possessed by the privacy information holder and the way to handle the data type; generating, using the user policy and a service policy set that includes at least one service policy in which a privacy information user describes at least one rule that is a pair of a data type of the privacy information and the way to handle the data type, a ranking of the service policy according to the degree of divergence between the user policy and the service policy; and displaying the service policy ranking on a privacy information holder terminal.

14 Claims, 29 Drawing Sheets

(51) Int. Cl.
*G06F 21/62* (2013.01)
*G06F 21/60* (2013.01)
*G06F 19/00* (2011.01)

(56) References Cited

U.S. PATENT DOCUMENTS

| | | | |
|---|---|---|---|
| 2004/0083243 A1* | 4/2004 | Feng et al. | 707/203 |
| 2005/0076233 A1* | 4/2005 | Aarts et al. | 713/201 |
| 2006/0143688 A1* | 6/2006 | Futoransky et al. | 726/1 |
| 2007/0006278 A1* | 1/2007 | Ioan Avram et al. | 726/1 |
| 2009/0193495 A1* | 7/2009 | McAfee et al. | 726/1 |
| 2009/0249430 A1* | 10/2009 | Buss et al. | 726/1 |
| 2010/0036779 A1* | 2/2010 | Sadeh-Koniecpol et al. | 706/11 |
| 2010/0153695 A1* | 6/2010 | Bussard et al. | 713/1 |
| 2011/0283335 A1* | 11/2011 | Bussard et al. | 726/1 |

FOREIGN PATENT DOCUMENTS

| | | | |
|---|---|---|---|
| JP | 2003-132160 A | 5/2003 | |
| JP | 2004-192353 A | 7/2004 | |
| JP | 2006-344156 A | 12/2006 | |
| JP | 2007-072582 A | 3/2007 | |
| JP | 2008-117026 A | 5/2008 | |

OTHER PUBLICATIONS

Makoto Hatakeyama et al., "Privacy Policy Negotiation Framework for Attribute Exchange", W3C Workshop on Languages for Privacy Policy Negotiation and Semantics—Driven Enforcement, 2006, [online], [searched on Feb. 23, 2011], the Internet <URL: http://www.w3.org/2006/07/privacy-ws/papers/22-hatakeyama-negotiation-attributes/>.
International Search Report of PCT/JP2012/055459 dated Mar. 27, 2012 English Translation.
Extended European Search Report dated Feb. 20, 2015 in corresponding European patent application No. 12751889.
Byers et al., "Searching for Privacy: Design and Implementation of a P3P-Enabled Search Engine," Jun. 9, 2005, pp. 314-328, cited in Extended European Search Report dated Feb. 20, 2015.
Communication dated May 21, 2015, issued by the State Intellectual Property Office of the People's Republic of China in corresponding Chinese Application No. 201280011223.7.

* cited by examiner

FIG. 6

```
<Policy>
  <Rule datatype="Name">
    <Action>
      PROVIDE
    </Action>
  </Rule>
  <Rule datatype="Address">
    <Action>
      DO NOT PROVIDE
    </Action>
  </Rule>
  <Rule datatype="Position">
    <Action>
      DO NOT PROVIDE
    </Action>
  </Rule>
  <Rule datatype="Buying">
    <Action>
      PROVIDE
    </Action>
  </Rule>
</Policy>
```

FIG. 7

```
<Policy>
  <Rule datatype="Name">
    <Action>
      ACQUIRE
    </Action>
  </Rule>
  <Rule datatype="Address">
    <Action>
      ACQUIRE
    </Action>
  </Rule>
  <Rule datatype="Position">
    <Action>
      ACQUIRE
    </Action>
  </Rule>
  <Rule datatype="Buying">
    <Action>
      DO NOT ACQUIRE
    </Action>
  </Rule>
</Policy>
```

FIG. 8

| SERVICE POLICY ID | SERVICE POLICY |
|---|---|
| 1 | <Policy><Rule datatype="Name"><Action>ACQUIRE</Action></Rule><Rule datatype="Address"><Action>ACQUIRE</Action></Rule><Rule datatype="Position"><Action>ACQUIRE</Action></Rule><Rule datatype="Buying"><Action>ACQUIRE</Action></Rule></Policy> |
| 2 | <Policy><Rule datatype="Name"><Action>ACQUIRE</Action></Rule><Rule datatype="Address"><Action>ACQUIRE</Action></Rule><Rule datatype="Position"><Action>ACQUIRE</Action></Rule><Rule datatype="Buying"><Action>DO NOT ACQUIRE</Action></Rule></Policy> |
| 3 | <Policy><Rule datatype="Name"><Action>ACQUIRE</Action></Rule><Rule datatype="Address"><Action>ACQUIRE</Action></Rule><Rule datatype="Position"><Action>DO NOT ACQUIRE</Action></Rule><Rule datatype="Buying"><Action>DO NOT ACQUIRE</Action></Rule></Policy> |
| 4 | <Policy><Rule datatype="Name"><Action>DO NOT ACQUIRE</Action></Rule><Rule datatype="Address"><Action>DO NOT ACQUIRE</Action></Rule><Rule datatype="Position"><Action>ACQUIRE</Action></Rule><Rule datatype="Buying"><Action>DO NOT ACQUIRE</Action></Rule></Policy> |
| 5 | <Policy><Rule datatype="Name"><Action>DO NOT ACQUIRE</Action></Rule><Rule datatype="Address"><Action>DO NOT ACQUIRE</Action></Rule><Rule datatype="Position"><Action>DO NOT ACQUIRE</Action></Rule><Rule datatype="Buying"><Action>ACQUIRE</Action></Rule></Policy> |

FIG. 10

NAME
- ○ SUBMIT
- ○ DO NOT SUBMIT

ADDRESS
- ○ SUBMIT
- ○ DO NOT SUBMIT

POSITION INFORMATION
- ○ SUBMIT
- ○ DO NOT SUBMIT

PURCHASE INFORMATION
- ○ SUBMIT
- ○ DO NOT SUBMIT

FIG. 12

| SERVICE POLICY ID | DISTANCE |
|---|---|
| 1 | 2 |
| 2 | 2 |
| 3 | 1 |
| 4 | 1 |
| 5 | 0 |

FIG. 13

| RANKING | SERVICE POLICY ID | SERVICE POLICY |
|---|---|---|
| 1 | 5 | <Policy><Rule datatype="Name"><Action>DO NOT ACQUIRE</Action></Rule><Rule datatype="Address"><Action>DO NOT ACQUIRE</Action></Rule><Rule datatype="Position"><Action>DO NOT ACQUIRE</Action></Rule><Rule datatype="Buying"><Action>ACQUIRE</Action></Rule></Policy> |
| 2 | 3 | <Policy><Rule datatype="Name"><Action>ACQUIRE</Action></Rule><Rule datatype="Address"><Action>ACQUIRE</Action></Rule><Rule datatype="Position"><Action>DO NOT ACQUIRE</Action></Rule><Rule datatype="Buying"><Action>DO NOT ACQUIRE</Action></Rule></Policy> |
| 2 | 4 | <Policy><Rule datatype="Name"><Action>DO NOT ACQUIRE</Action></Rule><Rule datatype="Address"><Action>DO NOT ACQUIRE</Action></Rule><Rule datatype="Position"><Action>ACQUIRE</Action></Rule><Rule datatype="Buying"><Action>DO NOT ACQUIRE</Action></Rule></Policy> |
| 4 | 1 | <Policy><Rule datatype="Name"><Action>ACQUIRE</Action></Rule><Rule datatype="Address"><Action>ACQUIRE</Action></Rule><Rule datatype="Position"><Action>ACQUIRE</Action></Rule><Rule datatype="Buying"><Action>ACQUIRE</Action></Rule></Policy> |
| 4 | 2 | <Policy><Rule datatype="Name"><Action>ACQUIRE</Action></Rule><Rule datatype="Address"><Action>ACQUIRE</Action></Rule><Rule datatype="Position"><Action>ACQUIRE</Action></Rule><Rule datatype="Buying"><Action>DO NOT ACQUIRE</Action></Rule></Policy> |

FIG. 14

RANKING 1 :
    NAME: DO NO ACQUIRE
    ADDRESS: DO NO ACQUIRE
    POSITION INFORMATION: DO NOT ACQUIRE
    PURCHASE INFORMATION: ACQUIRE

[SELECT]

RANKING 2 :
    NAME: ACQUIRE
    ADDRESS: ACQUIRE
    POSITION INFORMATION: DO NOT ACQUIRE
    PURCHASE INFORMATION: DO NOT ACQUIRE

[SELECT]

RANKING 3:
    NAME: DO NOT ACQUIRE
    ADDRESS: DO NOT ACQUIRE
    POSITION INFORMATION: ACQUIRE
    PURCHASE INFORMATION: DO NOT ACQUIRE

[SELECT]

RANKING 4 :
    . . .

FIG. 15

| USER ID | SERVICE POLICY ID |
|---------|-------------------|
| 1 | 5 |
| 2 | 3 |
| 3 | 2 |
| 4 | 2 |

FIG. 17

| SERVICE POLICY ID | SERVICE CONTENT | SERVICE POLICY |
|---|---|---|
| 1 | HIGHLY ACCURATE RECOMMENDATIONS AND CONSISTENT EC SERVICES | <Policy><Rule datatype="Name"><Action>ACQUIRE</Action></Rule><Rule datatype="Address"><Action>ACQUIRE</Action></Rule><Rule datatype="Position"><Action>ACQUIRE</Action></Rule><Rule datatype="Buying"><Action>ACQUIRE</Action></Rule></Policy> |
| 2 | RECOMMENDATIONS BASED ON POSITION INFORMATION AND CONSISTENT EC SERVICES | <Policy><Rule datatype="Name"><Action>ACQUIRE</Action></Rule><Rule datatype="Address"><Action>ACQUIRE</Action></Rule><Rule datatype="Position"><Action>ACQUIRE</Action></Rule><Rule datatype="Buying"><Action>DO NOT ACQUIRE</Action></Rule></Policy> |
| 3 | EC SERVICES; NO RECOMMENDATIONS | <Policy><Rule datatype="Name"><Action>ACQUIRE</Action></Rule><Rule datatype="Address"><Action>ACQUIRE</Action></Rule><Rule datatype="Position"><Action>DO NOT ACQUIRE</Action></Rule><Rule datatype="Buying"><Action>DO NOT ACQUIRE</Action></Rule></Policy> |
| 4 | RECOMMENDATIONS BASED ON POSITION INFORMATION | <Policy><Rule datatype="Name"><Action>DO NOT ACQUIRE</Action></Rule><Rule datatype="Address"><Action>DO NOT ACQUIRE</Action></Rule><Rule datatype="Position"><Action>ACQUIRE</Action></Rule><Rule datatype="Buying"><Action>DO NOT ACQUIRE</Action></Rule></Policy> |
| 5 | RECOMMENDATIONS BASED ON PURCHASE INFORMATION | <Policy><Rule datatype="Name"><Action>DO NOT ACQUIRE</Action></Rule><Rule datatype="Address"><Action>DO NOT ACQUIRE</Action></Rule><Rule datatype="Position"><Action>DO NOT ACQUIRE</Action></Rule><Rule datatype="Buying"><Action>ACQUIRE</Action></Rule></Policy> |

FIG. 19

| RANKING | SERVICE POLICY ID | SERVICE CONTENT | POLICY DIFFERENCE |
|---|---|---|---|
| 1 | 5 | RECOMMENDATIONS BASED ON PURCHASE INFORMATION | NONE |
| 2 | 3 | EC SERVICES; NO RECOMMENDATIONS | ACQUIRE "ADDRESS" THAT USER DOES NOT WANT TO PROVIDE |
| 2 | 4 | RECOMMENDATIONS BASED ON POSITION INFORMATION | MUST PROVIDE "POSITION" THAT USER DOES NOT WANT TO PROVIDE |
| 4 | 1 | HIGHLY ACCURATE RECOMMENDATIONS AND CONSISTENT EC SERVICES | ACQUIRE "ADDRESS" THAT USER DOES NOT WANT TO PROVIDE MUST PROVIDE "POSITION" THAT USER DOES NOT WANT TO PROVIDE |
| 4 | 2 | RECOMMENDATIONS BASED ON POSITION INFORMATION AND CONSISTENT EC SERVICES | ACQUIRE "ADDRESS" THAT USER DOES NOT WANT TO PROVIDE MUST PROVIDE "POSITION" THAT USER DOES NOT WANT TO PROVIDE |

FIG. 22

```
<Policy>
  <Rule datatype="Name">
    <Action>
      PROVIDE
    </Action>
  </Rule>
  <Rule datatype="Address">
    <Action>
      DO NOT PROVIDE
    </Action>
  </Rule>
  <Rule datatype="Position">
    <Action>
      PROTECT
    </Action>
  </Rule>
  <Rule datatype="Buying">
    <Action>
      PROVIDE
    </Action>
  </Rule>
</Policy>
```

FIG. 23

| SERVICE POLICY ID | SERVICE POLICY |
|---|---|
| 1 | <Policy><Rule datatype="Name"><Action>ACQUIRE</Action></Rule><Rule datatype="Address"><Action>ACQUIRE</Action></Rule><Rule datatype="Position"><Action>ACQUIRE</Action></Rule><Rule datatype="Buying"><Action>ACQUIRE</Action></Rule></Policy> |
| 2 | <Policy><Rule datatype="Name"><Action>ACQUIRE</Action></Rule><Rule datatype="Address"><Action>ACQUIRE</Action></Rule><Rule datatype="Position"><Action>ACQUIRE</Action></Rule><Rule datatype="Buying"><Action>PROTECT</Action></Rule></Policy> |
| 3 | <Policy><Rule datatype="Name"><Action>ACQUIRE</Action></Rule><Rule datatype="Address"><Action>ACQUIRE</Action></Rule><Rule datatype="Position"><Action>PROTECT</Action></Rule><Rule datatype="Buying"><Action>DO NOT ACQUIRE</Action></Rule></Policy> |
| 4 | <Policy><Rule datatype="Name"><Action>DO NOT ACQUIRE</Action></Rule><Rule datatype="Address"><Action>DO NOT ACQUIRE</Action></Rule><Rule datatype="Position"><Action>ACQUIRE</Action></Rule><Rule datatype="Buying"><Action>DO NOT ACQUIRE</Action></Rule></Policy> |
| 5 | <Policy><Rule datatype="Name"><Action>PROTECT</Action></Rule><Rule datatype="Address"><Action>DO NOT ACQUIRE</Action></Rule><Rule datatype="Position"><Action>DO NOT ACQUIRE</Action></Rule><Rule datatype="Buying"><Action>ACQUIRE</Action></Rule></Policy> |

FIG. 26

| ACTION | PROTECTION VECTOR |
|---|---|
| DO NOT PROVIDE | (1) |
| PROVIDE | (0) |
| DO NOT ACQUIRE | (1) |
| ACQUIRE | (0) |
| PROTECT | (0.5) |

FIG. 27

| SERVICE POLICY ID | DATA TYPE | PROTECTION VECTOR |
|---|---|---|
| 1 | Name | (0) |
|   | Address | (0) |
|   | Position | (0) |
|   | Buying | (0) |
| 2 | Name | (0) |
|   | Address | (0) |
|   | Position | (0) |
|   | Buying | (0.5) |
| 3 | Name | (0) |
|   | Address | (0) |
|   | Position | (0.5) |
|   | Buying | (1) |
| 4 | Name | (1) |
|   | Address | (1) |
|   | Position | (0) |
|   | Buying | (1) |
| 5 | Name | (0.5) |
|   | Address | (1) |
|   | Position | (1) |
|   | Buying | (0) |

FIG. 29

| SERVICE POLICY ID | DISTANCE |
|---|---|
| 1 | 1.5 |
| 2 | 1.5 |
| 3 | 1 |
| 4 | 0.5 |
| 5 | 0 | ically/semi-automatically made.

POLICY ARBITRATION METHOD, POLICY ARBITRATION SERVER, AND PROGRAM

REFERENCE TO RELATED APPLICATION

This is a National Stage of International Application No. PCT/JP2012/055459 filed Mar. 2, 2012, claiming the benefit of the priority of Japanese Patent Application No. 2011-045911 filed on Mar. 3, 2011, the disclosures of all of which are incorporated herein in their entirety by reference thereto.

TECHNICAL FIELD

The present invention relates to a policy arbitration method, a policy arbitration server, and a program, and particularly to a policy arbitration method, a policy arbitration server, and a program that resolve a conflict between a privacy information holder's policy regarding how his privacy information is handled and a policy of a user of the privacy information regarding how the privacy information is used.

BACKGROUND

In recent years, services that obtain attribute information (age, sex, address, etc.) and activity information (location information, purchase information, etc.) of a privacy information holder to utilize the information for delivering advertisements of interest to the privacy information holder have attracted attention.

In such a service, since the attribute information and the activity information are privacy information, the privacy of a privacy information holder will be violated if a privacy information user, who provides the service, unilaterally acquires and utilizes the privacy information. Therefore, a privacy information holder needs to be able to control how a privacy information user handles privacy information (disclosure requirements, data protection requirements, etc.).

As a method for performing such control, Non-Patent Literature (NPL) 1 describes a policy-based control method using P3P (Platform for Privacy Preferences).

In P3P, privacy information collected by a privacy information user (service provider) and the way this information is handled are set as a policy file (referred to as "service policy" hereinafter) written in XML (Extensible Markup Language), and by investigating whether or not conditions of data disclosure match between a policy file (referred to as "user policy" hereinafter) describing a data disclosure policy set in advance by a privacy information holder and the aforementioned service policy, a data disclosure decision can be automatically/semi-automatically made.

P3P has a problem that a privacy information user cannot use the data and a privacy information holder cannot receive a service when a conflict arises between the user policy and the service policy and data disclosure agreement cannot be reached (for instance, when there is a conflict between the two policies regarding the conditions of data disclosure). Therefore, policy agreement must be reached between the privacy information holder and the privacy information user. Such a method for reaching policy agreement between two parties is called policy arbitration method.

Patent Literature (PTL) 1 describes an example of the policy arbitration method. The policy arbitration method in Patent Literature 1 is constituted by privacy information holder terminals connected to each other via a network, a privacy information user terminal, and a server.

According to Patent Literature 1, each of the privacy information holder terminals registers a privacy policy defining standards for using privacy information to the server, the privacy information user terminal registers a user policy defining a range of requirements for privacy information disclosure to the server, the server determines whether or not there is a conflict between the policies, and the server notifies the privacy information holder terminal of the user policy when there is a conflict, requesting consent for privacy information disclosure. When there is no conflict and when consent is made, the privacy information user terminal is able to use the privacy information.

Further, Non-Patent Literature 2 describes another example of a policy arbitration method. The policy arbitration method in Non-Patent Literature 2 is constituted by privacy information holder terminals and privacy information user terminals connected by a network.

According to Non-Patent Literature 2, a privacy information user terminal transmits a user policy to a privacy information holder terminal, and the privacy information holder terminal compares the user policy to a privacy policy and transmits attribute information of the privacy information holder if there is no conflict. Further, when there is a conflict, a user transmits use/preservation conditions to the privacy information user terminal from the privacy information holder terminal, and the privacy information user terminal creates a new user policy meeting these conditions and transmits the new policy to the privacy information holder terminal. In other words, policy arbitration is performed by repeating the transmission of the user policy, the comparison, the transmission of conditions, and the creation of a new policy until agreement between the two parties is reached.

Patent Literatures 2 to 4 are other relevant documents.
PTL 1:
Japanese Patent Kokai Publication No. JP2004-192353A
PTL 2:
Japanese Patent Kokai Publication No. JP2003-132160A
PTL 3:
Japanese Patent Kokai Publication No. JP2006-344156A
PTL 4:
Japanese Patent Kokai Publication No. JP2008-117026A
NPL 1:
Platform for Privacy Preferences (P3P) Project, [online], [searched on Feb. 23, 2011], the Internet <URL: http://www.w3.org/P3P/>.
NPL 2:
Hatakeyama, M., Gomi, H., "Privacy Policy Negotiation Framework for Attribute Exchange", W3C Workshop on Languages for Privacy Policy Negotiation and Semantics—Driven Enforcement, 2006, [online], [searched on Feb. 23, 2011], the Internet <URL: http://www.w3.org/2006/07/privacy-ws/papers/22-hatakeyama-negotiation-attributes/>.

SUMMARY

The entire disclosures of the above mentioned Patent Literatures and Non-Patent Literatures are incorporated herein by reference thereto. The following analysis is given by the present invention. The policy arbitration method described in Patent Literature 1 is able to perform policy arbitration with only one interaction, however, even when there is a conflict between the user policy and the service policy, the privacy information holder has no choice but to agree to the service policy in order to receive the service. As a result, there is no option in terms of changing the quality of the service offered according to the degree of the privacy information provided such as a case where a better service will be offered if a certain piece of data is additionally provided, and policy agreement cannot be flexibly reached.

Meanwhile, in the policy arbitration method described in Non-Patent Literature 2, a privacy information holder and privacy information user can flexibly reach policy agreement by performing a plurality of interactions between the privacy information holder and the privacy information user. However, it is inefficient for the privacy information user to perform a plurality of interactions for a single privacy information holder.

Therefore, there is a need in the art to provide a policy arbitration method capable of flexibly facilitating policy agreement between a privacy information holder and privacy information user while reducing the number of interactions.

According to a first aspect of the present invention, there is provided a policy arbitration method. The policy arbitration method comprises: entering a user policy in which a privacy information holder describes at least one rule that is a pair of a data type of privacy information possessed by the privacy information holder and the way to handle the data type; generating, using the user policy and a service policy set that includes at least one service policy in which a privacy information user describes at least one rule that is a pair of a data type of the privacy information and the way to handle the data type, a ranking of the service policy according to the degree of divergence between the user policy and the service policy; and displaying the service policy ranking on a privacy information holder terminal The policy arbitration method may further comprise having the privacy information holder select one service policy from the service policy ranking. The present method is tied to a particular machine, which is a computer that handles privacy information of a privacy information holder.

According to a second aspect of the present invention, there is provided an arbitration server. The arbitration server comprises: a user policy receiving unit that receives from a user a user policy describing at least one rule that is a pair of a data type of privacy information possessed by the user and the way to handle the data type; and a ranking generation unit that generates, using the user policy and a service policy set that includes at least one service policy describing at least one rule that is a pair of a data type of the privacy information and the way to handle the data type, a ranking of the service policy based on the degree of divergence between the user policy and the service policy. The arbitration server may further comprise an agreed policy receiving unit that receives from the user who has referred to the service policy ranking selection of a service policy to be applied to the privacy information of the user.

According to a third aspect of the present invention, there is provided a program. The program causes an arbitration server to execute: receiving from a user a user policy describing at least one rule that is a pair of a data type of privacy information possessed by the user and the way to handle the data type; and generating, using the user policy and a service policy set that includes at least one service policy describing at least one rule that is a pair of a data type of the privacy information and the way to handle the data type, a ranking of the service policy based on the degree of divergence between the user policy and the service policy. The program may further cause the arbitration server to execute receiving from the user who has referred to the service policy ranking selection of a service policy to be applied to the privacy information of the user. Further, this program can be stored in a computer-readable recording-medium. In other words, the present invention can be realized as a computer program product as well.

The present invention provides the following advantage, but not restricted thereto. According to the present invention, it becomes possible to flexibly facilitate policy agreement between a privacy information holder and privacy information user while reducing the number of interactions.

BRIEF DESCRIPTION OF THE DRAWINGS

FIG. 6 is an example of a user policy used to describe an operation of the first exemplary embodiment of the present invention.

FIG. 7 is an example of a service policy used to describe an operation of the first exemplary embodiment of the present invention.

FIG. 8 is a drawing showing a storage format of service policies in a service policy storage unit in FIG. 4.

FIG. 10 is an example of a user policy input screen displayed by a user policy input unit in FIG. 4.

FIG. 12 is a drawing showing the results of calculation by the policy distance calculation unit in FIG. 5.

FIG. 13 is an example of service policy rankings generated by the ranking generation unit in FIG. 4.

FIG. 14 is an example of a service policy ranking display screen displayed by a ranking display unit in FIG. 4.

FIG. 15 is a drawing showing a storage format of agreed policies in an agreed policy storage unit in FIG. 4.

FIG. 17 is a drawing showing a storage format of service policies in a service policy storage unit of the arbitration server of the second exemplary embodiment of the present invention.

FIG. 19 is an example of service policy rankings generated by the ranking generation unit of the arbitration server of the second exemplary embodiment of the present invention.

FIG. 22 is an example of a user policy used to describe an operation of the third exemplary embodiment of the present invention.

FIG. 23 is a drawing showing a storage format of service policies in a service policy storage unit of the arbitration server of the third exemplary embodiment of the present invention.

FIG. 26 is an example of information stored in an action information storage unit used to describe an operation of the third exemplary embodiment of the present invention.

FIG. 27 is a drawing showing a state after the service policies have been mapped by the policy mapping unit of the arbitration server of the third exemplary embodiment of the present invention.

FIG. 29 is a drawing showing the results of calculating the distance to the service policies performed by the vector distance calculation unit of the arbitration server of the third exemplary embodiment of the present invention.

PREFERRED MODES

Figure 1:
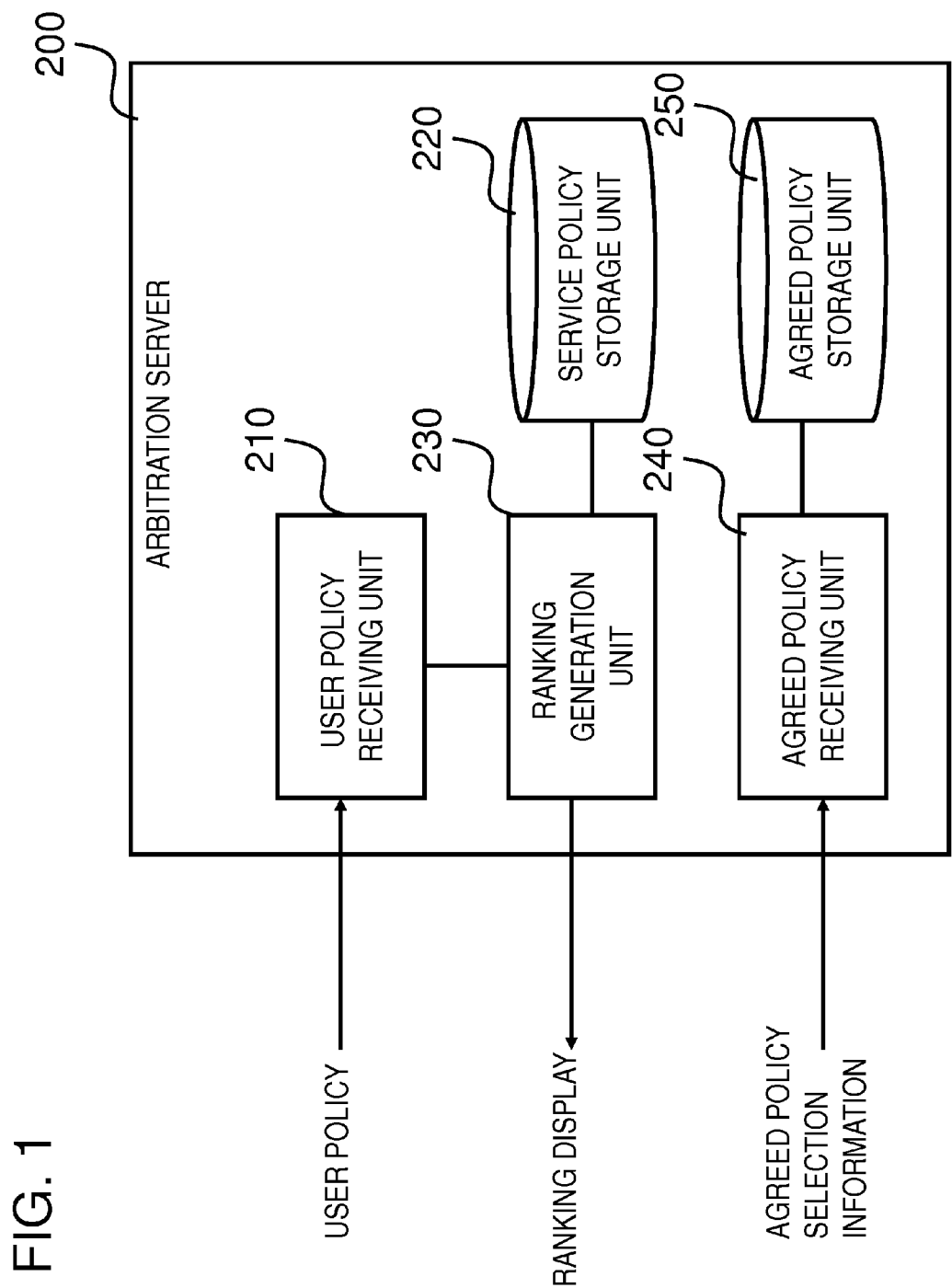
FIG. 1 is a drawing for explaining a summary of the present invention.

In the present disclosure, there are various possible modes, which include the following, but not restricted thereto. First, a summary of an exemplary embodiment of the present invention will be described with reference to the drawings. Note that the drawing reference signs used in the summary are given to elements as an example for convenience to facilitate understanding and not to limit the present invention to the illustrated aspects.

Referring to FIG. 1, The present invention, in an exemplary embodiment thereof, can be realized by an arbitration server 200 comprising a user policy receiving unit 210 for receiving a user policy supplied by a privacy information holder (simply referred to as "user" hereinafter); a service policy storage unit 220 for storing at least one service policy describing at least one rule which is a set of a data type and an action desired by a privacy information user; a ranking generation unit 230 for generating a service policy ranking of the service policy in the order of the degree of divergence (smallest to largest) between the supplied user policy and at least one service policy; an agreed policy receiving unit 240 for receiving a service policy (also referred to as "agreed policy" hereinafter) selected by the user as an accepted policy from the service policies; and an agreed policy storage unit 250 for storing the agreed policy.

Further, the user policy and the service policy describes a data type (value identifying the property of data such as name, age, etc.) and an action for each data type (how to handle privacy information such as whether or not the disclosure of the data is allowed, whether or not the information should be acquired, a privacy protection process is performed, etc.).

Figure 2:
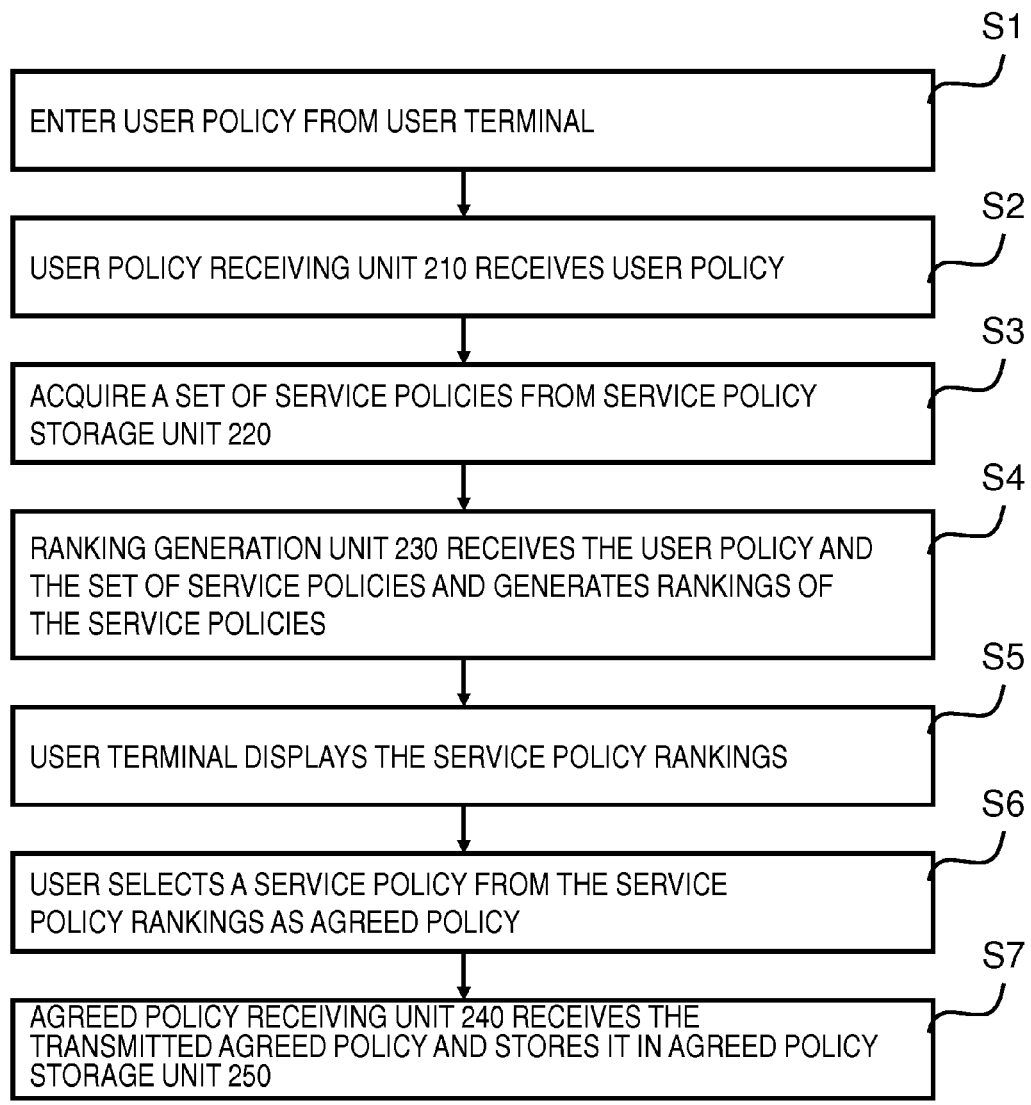
FIG. 2 is a flowchart for explaining a summary of the present invention.

The arbitration server operates as shown in FIG. 2. First, a privacy information holder enters a user policy using his own terminal (referred to as "user terminal" hereinafter) (step S1).

Next, the user policy receiving unit 210 of the arbitration server 200 receives the user policy (step S2).

Next, the ranking generation unit 230 acquires a set of service policies from the service policy storage unit 220 (step S3).

Next, the ranking generation unit 230 receives the user policy and the set of service policies, generates rankings of the service policies based on the degree of divergence between the user policy and the service policies, and transmits the service policy rankings to the user terminal (step S4).

The generated service policy rankings are displayed on the user terminal (step S5). The user selects a service policy from the service policy rankings displayed, and transmits the selected policy to the arbitration server 200 as an agreed policy (step S6).

Finally, the agreed policy receiving unit 240 receives the agreed policy and stores it in the agreed policy storage unit 250 (step S7).

Further, in the step S6, the user may be able to choose not to receive the service if he cannot select any agreed policy from the service policy rankings or there is no service policy he wants to select.

Figure 3:
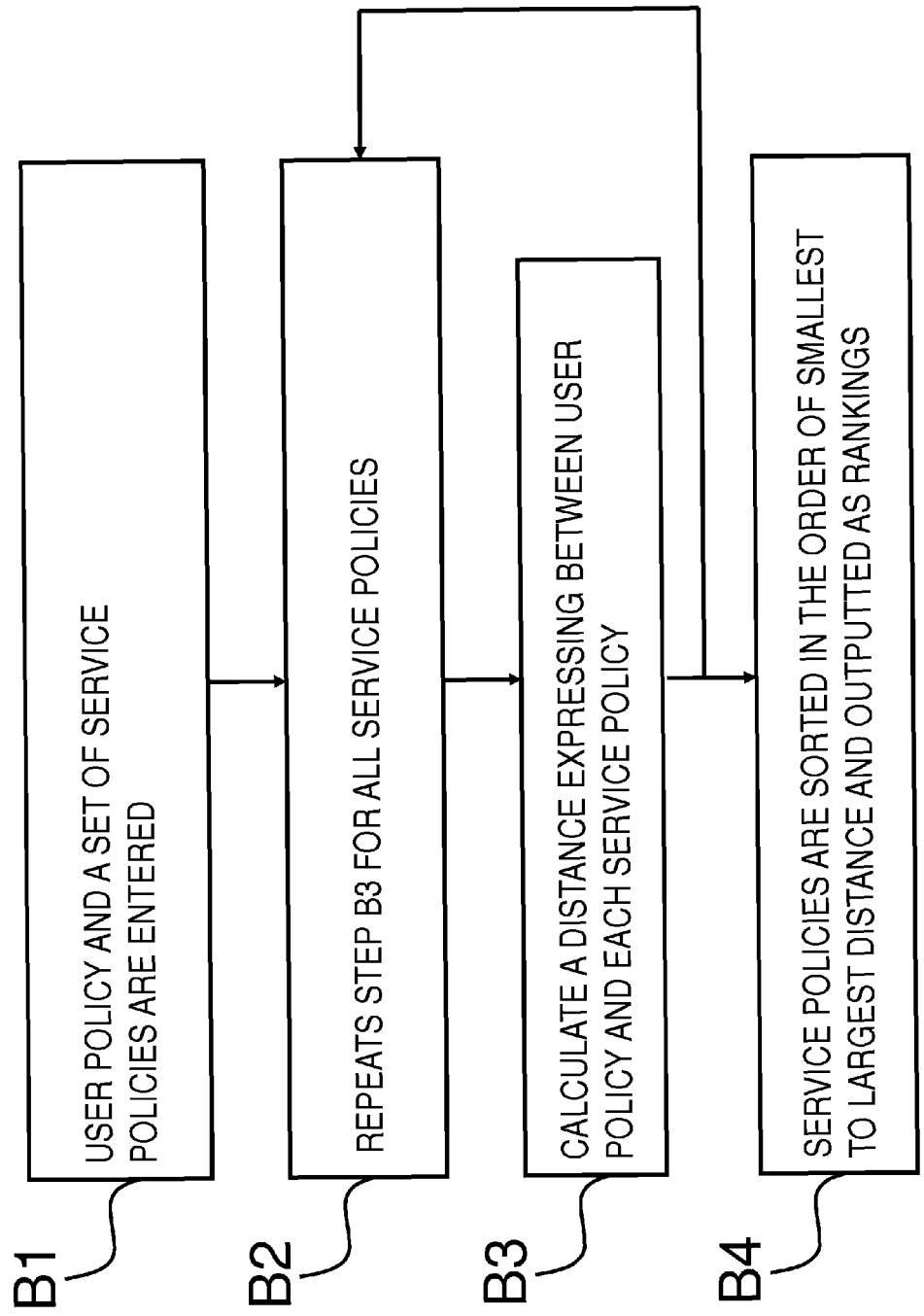
FIG. 3 is a flowchart showing details of step S4 in FIG. 2.

The process of generating service policy rankings in the step S4 will be described with reference to FIG. 3.

First, the user policy received in the step S2 and the set of service policies acquired in the step S3 are entered into the ranking generation unit 230 (step B1).

Next, the ranking generation unit 230 repeats step B3 for all the service policies (step B2).

The ranking generation unit 230 calculates a distance expressing the degree of divergence between the user policy and each service policy (the step B3). For instance, this distance can be derived by expressing the difference in the handling of data between the user policy and a service policy as a numerical value for each data type and summing the differences in the handling of the data for all the data attributes. Further, in the calculation of the distance, a weighting may be appropriately performed for each data type.

Finally, the service policies are sorted in the order of smallest to largest distance and outputted as the service policy rankings (step B4).

As described, service policy rankings generated based on the distance between a user policy entered by a user and service policies determined by a privacy information user are provided to the user, enabling the user to select an agreed policy he can accept. As a result, as shown in FIG. 1, an agreed policy desirable for both the privacy information holder and the privacy information user can be generated by having the two parties perform only one interaction.

First Exemplary Embodiment

Figure 4:
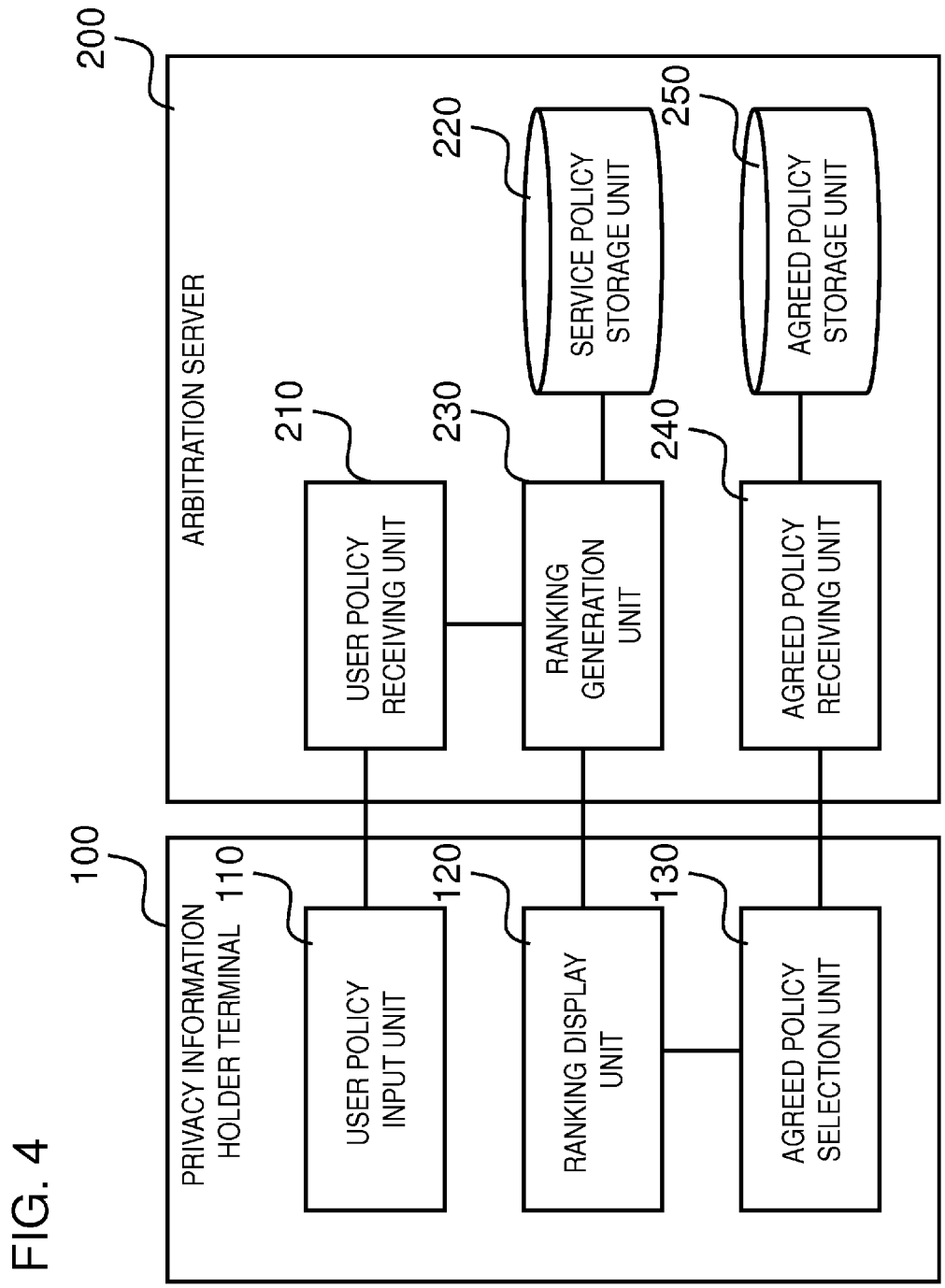
FIG. 4 is a block diagram showing a configuration of a first exemplary embodiment of the present invention.

Next, a first exemplary embodiment of the present invention will be described in detail with reference to the drawings. FIG. 4 is a block diagram showing a configuration of the first exemplary embodiment of the present invention. With reference to FIG. 4, a configuration including a privacy information holder terminal 100 and the arbitration server 200 is shown.

The privacy information holder terminal 100 comprises a user policy input unit 110 for entering a user policy, a ranking display unit 120 for displaying rankings of service policies, and an agreed policy selection unit 130 for selecting an agreed policy from service policy rankings.

The arbitration server 200 comprises the service policy storage unit 220 for storing a service policy ID identifying a service policy and a service policy, the user policy receiving unit 210 for receiving a user policy entered by a privacy information holder, the ranking generation unit 230 for generating service policy rankings based on the distance between the user policy and the service policies stored in the service policy storage unit 220, the agreed policy receiving unit 240 for receiving an agreed policy selected by the privacy information holder, and the agreed policy storage unit 250 for storing a user ID of the privacy information holder and the agreed policy.

Figure 5:
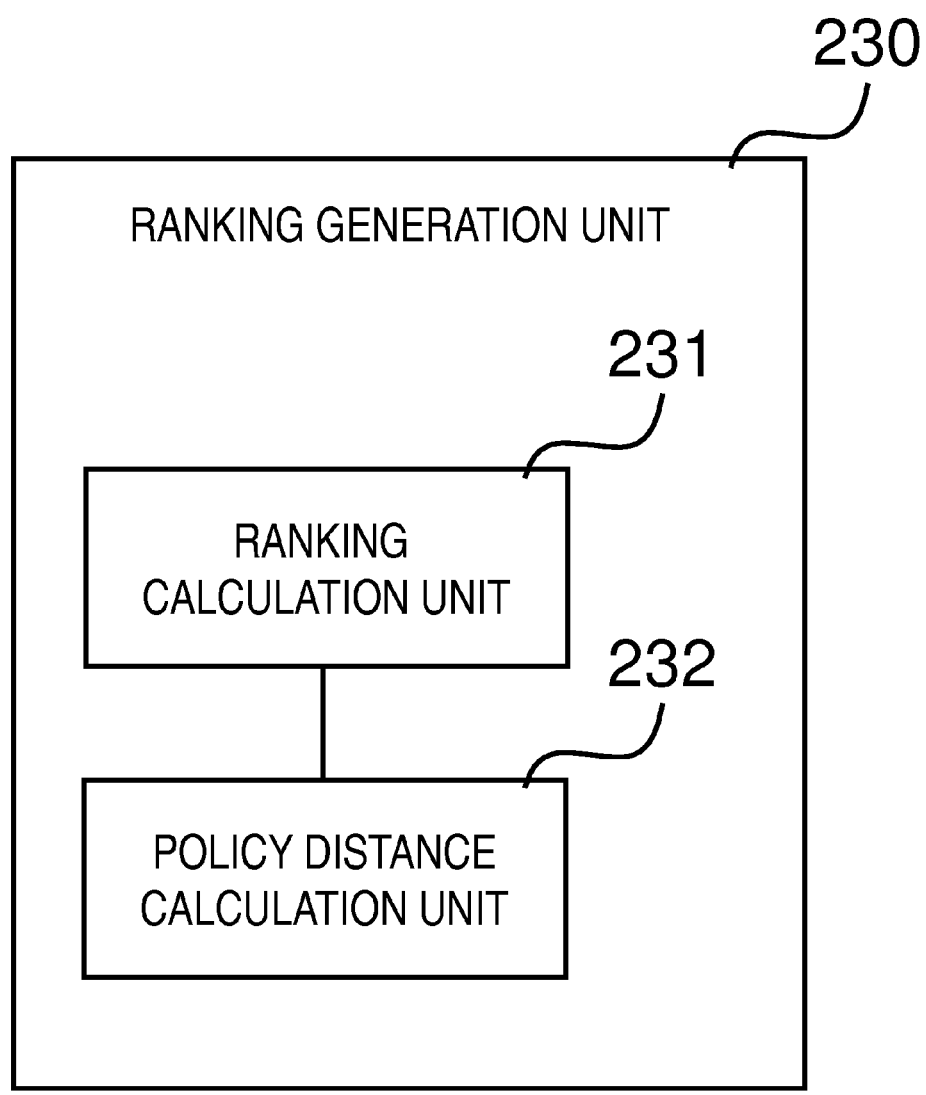
FIG. 5 is a block diagram showing a detailed configuration of a ranking generation unit in FIG. 4.

Further, as shown in FIG. 5, the ranking generation unit 230 includes a policy distance calculation unit 232 for calculating the distance between policies, which is the degree of divergence between the user policy and a service policy, and a ranking calculation unit 231 for ranking the service policies based on the distance between the policies.

In the exemplary embodiments below, the user policy is assumed to be written in XML in such a manner that binary values ("Provide" and "Do not provide") are set using ACTION tags as the content of a rule defining how each data type (datatype) such as Name and Address is handled, as shown in FIG. 6.

Further, the service policy is also assumed to be written in XML in such a manner that binary values ("Acquire" and "Do not acquire") are set using ACTION tags as the content of a rule defining how each data type (datatype) such as Name and Address is handled, as shown in FIG. 7.

Further, in the present exemplary embodiment, a conflict between the user policy and the service policy, described above, occurs when "not provided" is written in the rule of a data type while "acquire" is written in the rule of the corresponding data type of the service policy.

Further, each part (processing means) of the arbitration server 200 shown in FIGS. 4 and 5 can be realized by a computer program having a computer that constitutes the arbitration server 200 execute each processing described below using the hardware thereof.

Next, an operation of the present exemplary embodiment will be described in detail with reference to the drawings. First, a privacy information holder is assumed to have been already authenticated as the privacy information holder of User ID="1." Further, the service policy storage unit 220 is assumed to store service policy IDs and service policies in a table shown in FIG. 8. The service policy IDs in FIG. 8 are the identifiers of service policies.

Figure 9:
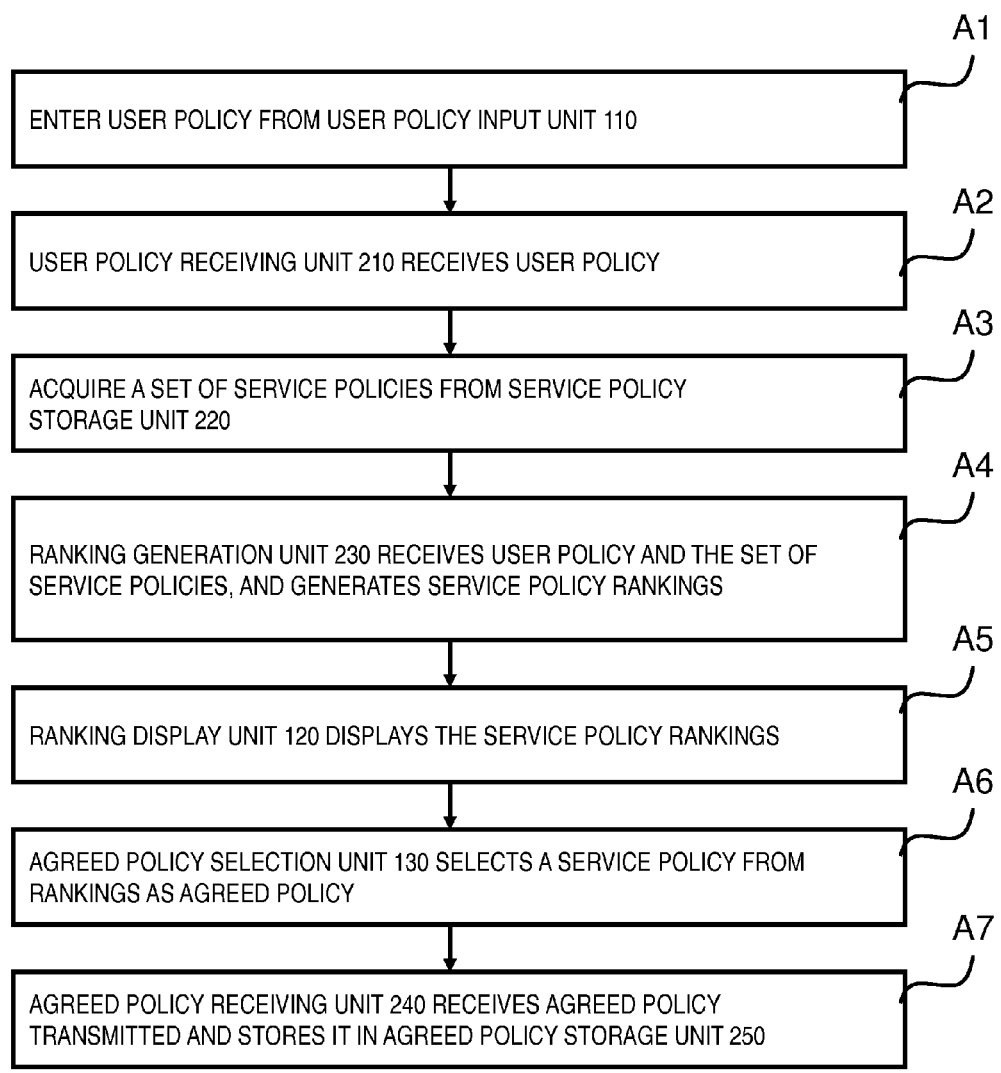
FIG. 9 is a flowchart showing an operation of the first exemplary embodiment of the present invention.

FIG. 9 is a flowchart showing an operation of the first exemplary embodiment of the present invention. With reference to FIG. 9, first, the user policy receiving unit 110 receives the entry of a user policy such as the one shown in FIG. 6 from the privacy information holder, and transmits it to the arbitration server 200 (step A1). FIG. 10 is an example of a user policy input screen displayed on the privacy information holder terminal 100 by the user policy input unit 110.

Next, the user policy receiving unit 210 of the arbitration server 200 receives the user policy from the privacy information holder terminal 110 (step A2).

Upon receiving the user policy, the ranking generation unit 230 of the arbitration server 200 acquires a set of service policies from the service policy storage unit 220 (step A3). In the present exemplary embodiment, five pairs of the service policy IDs ("1," "2," "3," "4," and "5") and the service policies written in XML are assumed to be acquired, as shown in FIG. 8.

Next, the ranking generation unit 230 generates service policy rankings (step A4).

With reference to the flowchart in FIG. 3 again, an operation in which the ranking generation unit 230 generates the service policy rankings will be described in detail.

First, the user policy (refer to FIG. 6) entered by the privacy information holder and the set of the pairs of the service policy IDs and the service policies (refer to FIG. 7) are entered into the ranking generation unit 230 (the step B1).

Next, the processing of the step B3 is performed on all the service policies (the step B2). More concretely, the distance between the user policy and a service policy that is the distance calculation target is calculated (the step B3).

Figure 11:
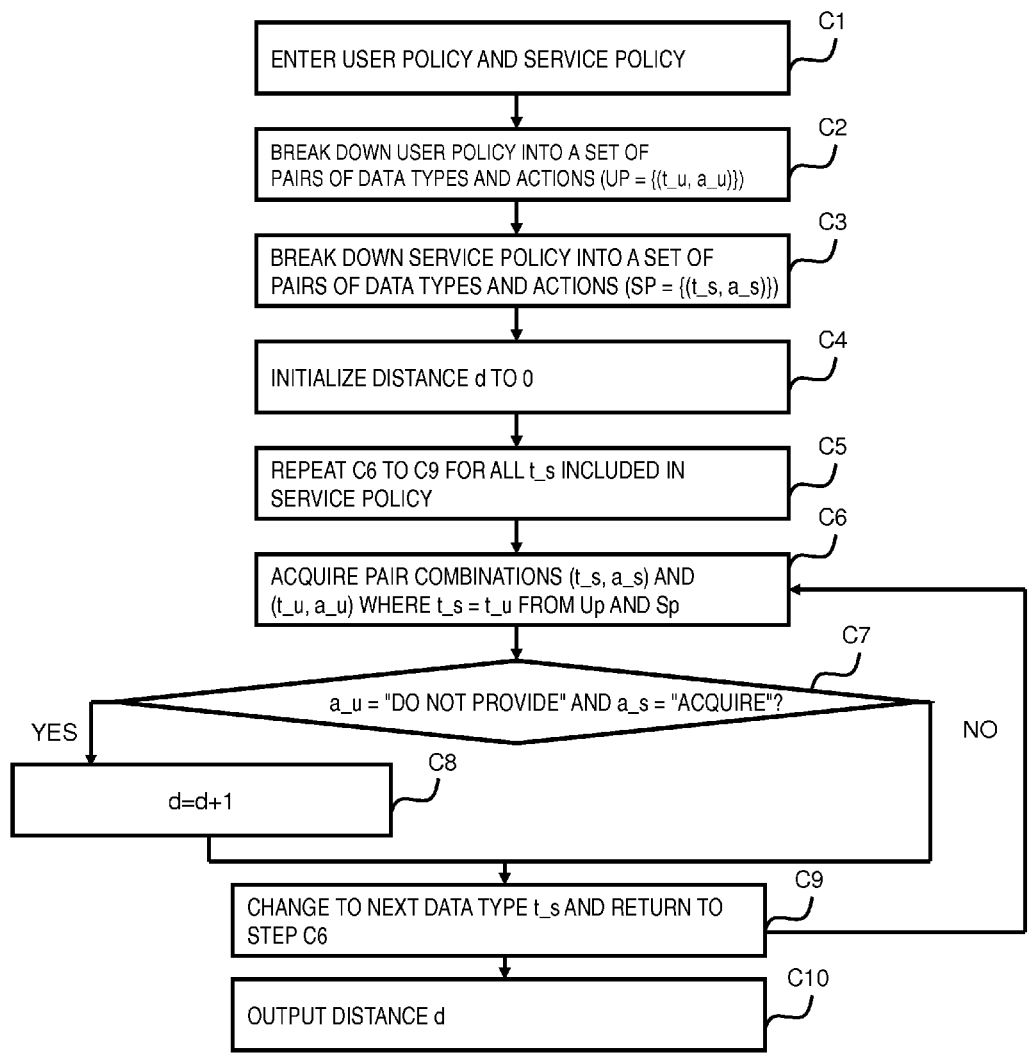
FIG. 11 is a flowchart showing an operation of a policy distance calculation unit in FIG. 5.

With reference to a flowchart in FIG. 11, the calculation of the distance between the user policy and the service policy performed by the policy distance calculation unit in the ranking generation unit 230 will be described in detail. In the description below, the distance between the user policy and the service policy is expressed by the number of conflicting rules.

First, the user policy and the service policy are entered (step C1). Here, the user policy shown in FIG. 6 and the service policy having the service policy ID "1" in FIG. 8 are assumed to be entered.

Next, the policy distance calculation unit 232 breaks down the user policy into a set of pairs of data types and actions (Up={(t_u, a_u)}) (step C2). For instance, in the case of the user policy in FIG. 6, a_u="Provide" for t_u="NAME," and it is ultimately broken down into Up={("NAME," "Provide"), ("Address," "Do not provide"), ("Position," "Do not provide"), ("Buying," "Provide")}.

Further, when a data type written in the service policy is not mentioned in the user policy, the policy distance calculation unit 232 treats this data type as having the action "Do not provide."

Next, the policy distance calculation unit 232 similarly breaks down the service policy into a set of pairs of data types and actions (Sp={(t_s, a_s)}) (step C3). For instance, in the case of the service policy having the service policy ID "1" in FIG. 8, a_s="Acquire" for t_s="NAME," and it is ultimately broken down into Sp={("NAME," "Acquire"), ("Address," "Acquire"), ("Position," "Acquire"), ("Buying," "Acquire")}.

Next, the policy distance calculation unit 232 initializes a distance d to zero (step C4). Further, the policy distance calculation unit 232 repeats steps C6 to C9 for all t_s={"NAME," "Address," "Position," "Buying"} included in the service policy Sp (step C5). Only an operation in the case of t_s="NAME" will be described below.

First, the policy distance calculation unit 232 acquires pair combinations (t_s, a_s) and (t_u, a_u) in which the data types match (t_s=t_u) from Up and Sp (the step C6). In the case of t_s="NAME," (t_s, a_s)=("NAME," "Provide"), (t_u, a_u)= ("NAME," "Acquire").

Next, the policy distance calculation unit 232 determines whether or not a_u="Do not provide" and a_s="Acquire" (the step C7).

Next, when the judgment above is YES, add one to the distance d (d=d+1) and the operation moves to the step C9 (the step C8). Meanwhile, when the judgment above is NO, the operation simply moves to the step C9. In the case of t_s="NAME," since a_u="Provide" and a_s="Acquire," the judgment is NO and the operation simply moves to the step C9.

Next, the policy distance calculation unit 232 changes the data type t_s and returns to the step C6 (the step C9).

After performing the steps C6 to C9 on all t_s, the policy distance calculation unit 232 outputs the distance d (step C10). In the case of the user policy in FIG. 6 and the service policy having the service policy ID "1," d=2 is ultimately outputted since the rules of the data types "Address" and "Position" conflict.

Figure 12:
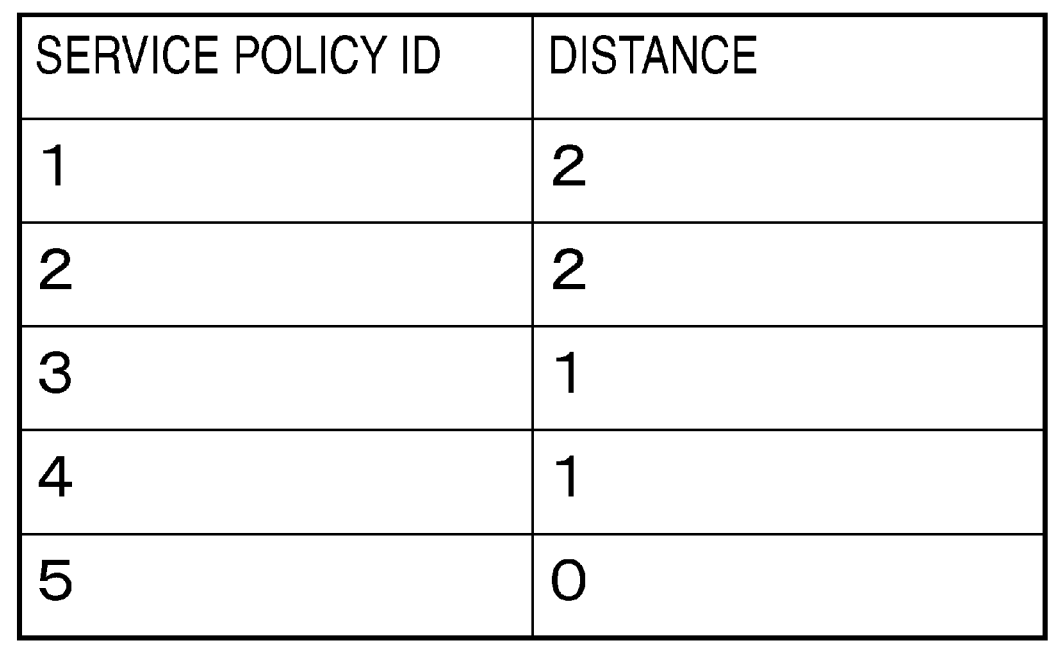

FIG. 12 is a drawing showing the results of calculating the distances between the user policy in FIG. 6 and all the service policies stored in the service policy storage unit 220 shown in FIG. 8.

With reference to FIG. 3 again, the ranking calculation unit 231 in the ranking generation unit 230 generates rankings by sorting the service policies in the order of smallest to largest distance d, and transmits the service policy rankings (a set of combinations of rankings, service policy IDs, and service policies) to the privacy information holder terminal 100 (the step B4).

FIG. 13 shows an example of the service policy rankings generated and sorted by the ranking calculation unit 231. As shown in FIG. 12, the service policy having the service policy ID "5" is displayed at the top since it has the smallest distance (d=0) to the user policy.

Next, the ranking display unit 120 receives and displays the service policy rankings. FIG. 14 is an example of the service policy rankings displayed by the ranking display unit 120 of the privacy information holder terminal 100 using the service policy rankings shown in FIG. 13.

Next, from the privacy information holder, the agreed policy selection unit 130 of the privacy information holder terminal 100 receives the selection of a service policy (agreed policy) applied to his privacy information from the service policy rankings. For instance, the agreed policy selection unit 130 can be realized by the selection buttons provided for the service policy rankings in FIG. 14 or input means for entering a service policy ID (not shown in the drawing).

For instance, if the privacy information holder selects the service policy in first place, the service policy ID "5" is transmitted to the arbitration server 200 as an agreed policy.

Figure 15:
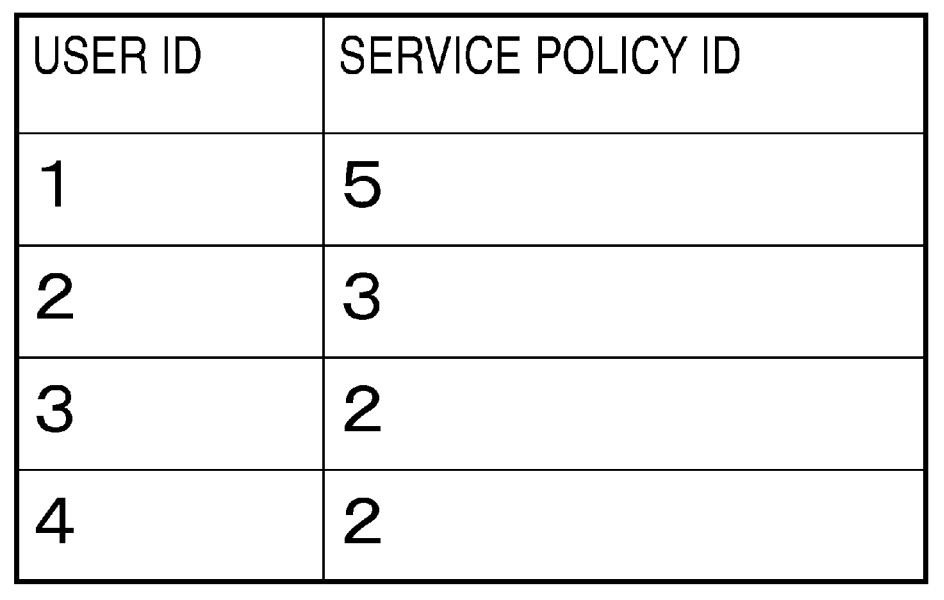

Finally, the agreed policy receiving unit 240 receives the agreed policy transmitted by the privacy information holder terminal 100 and stores it in the agreed policy storage unit 250. FIG. 15 is a drawing showing a state in which the selected agreed policy is stored in the agreed policy storage unit 250, and the service policy ID "5" is registered as the agreed policy of the privacy information holder having the user ID "1."

As described, in the present exemplary embodiment, it becomes possible to lead the user to agree to an agreed policy that he feels the most comfortable with by presenting rankings using the degree of divergence between the user policy entered by the privacy information holder using the user policy input unit 110 and the service policies entered by the privacy information user in advance. Further, in the present exemplary embodiment, the total number of data types having "Do not provide" written in the user policy and "Acquire" in the service policy is calculated as the distance between the policies, however, it is possible to calculate the distance by weighting a particular data type containing sensitive private information so as to increase the distance.

Second Exemplary Embodiment

Next, a second exemplary embodiment of the present invention, in which the configuration of the ranking generation unit 230 in the first exemplary embodiment is changed so as to be able to present reference information for the selection of an agreed policy, will be described in detail with reference to the drawings. The differences from the first exemplary embodiment will be mainly explained below.

Figure 16:
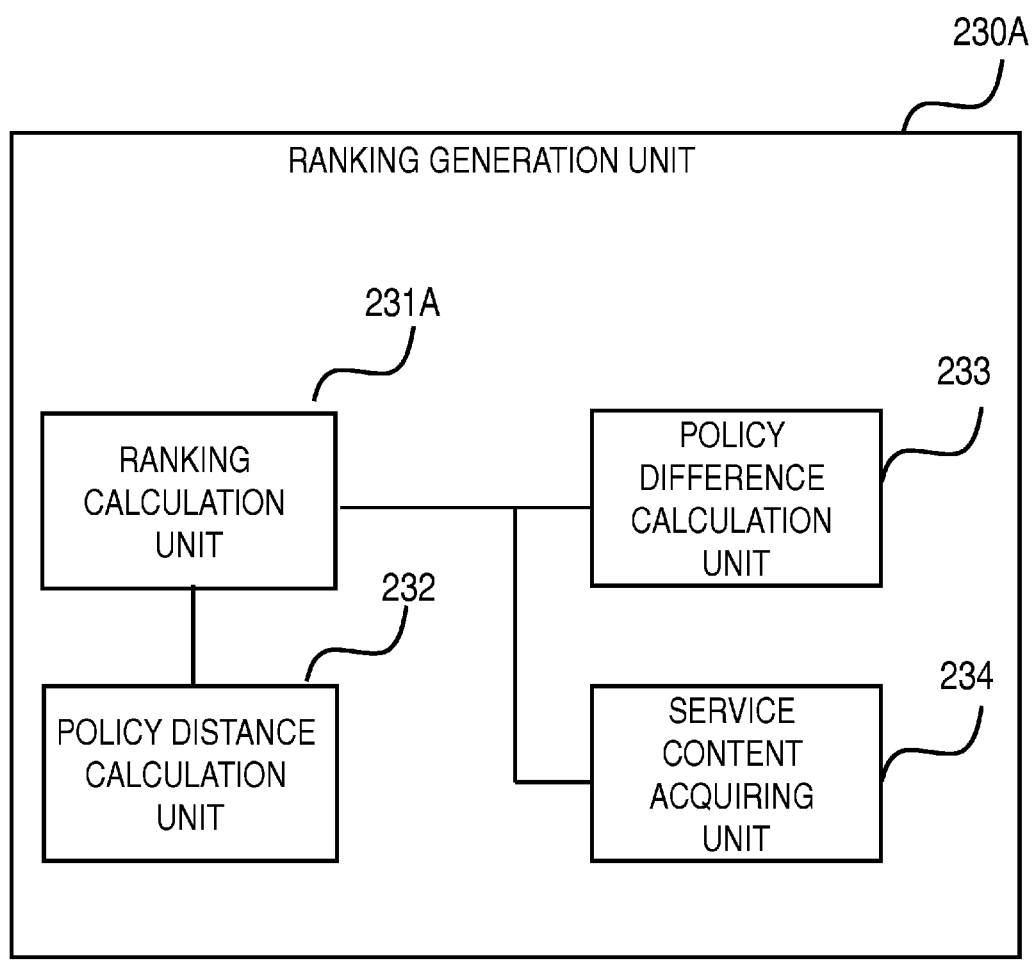
FIG. 16 is a block diagram showing a detailed configuration of a ranking generation unit of an arbitration server of a second exemplary embodiment of the present invention.

FIG. 16 is a block diagram showing a configuration of a ranking generation unit 230A provided in an arbitration server of the second exemplary embodiment of the present invention. With reference to FIG. 16, a policy difference calculation unit 233 and a service content acquiring unit 234 are newly added to the ranking generation unit 230 in the first exemplary embodiment.

The policy difference calculation unit 233 drives an explanation regarding conflicting rules between a user policy and service policy.

The service content acquiring unit 234 acquires an explanation regarding the service provided by each service policy.

The ranking calculation unit 231A of the present exemplary embodiment transmits service policy rankings, to which information sent from the policy difference calculation unit 233 and the service content acquiring unit 234 is added, to the privacy information holder terminal 100.

FIG. 17 is an example of a service policy storage table stored in the service policy storage unit of the arbitration server 200 of the present exemplary embodiment. This table differs from the table of the first exemplary embodiment, shown in FIG. 8, in that fields describing the service content are added. The service content acquiring unit 234 acquires an explanation regarding the service provided by each service policy from these fields describing the service content.

Figure 18:
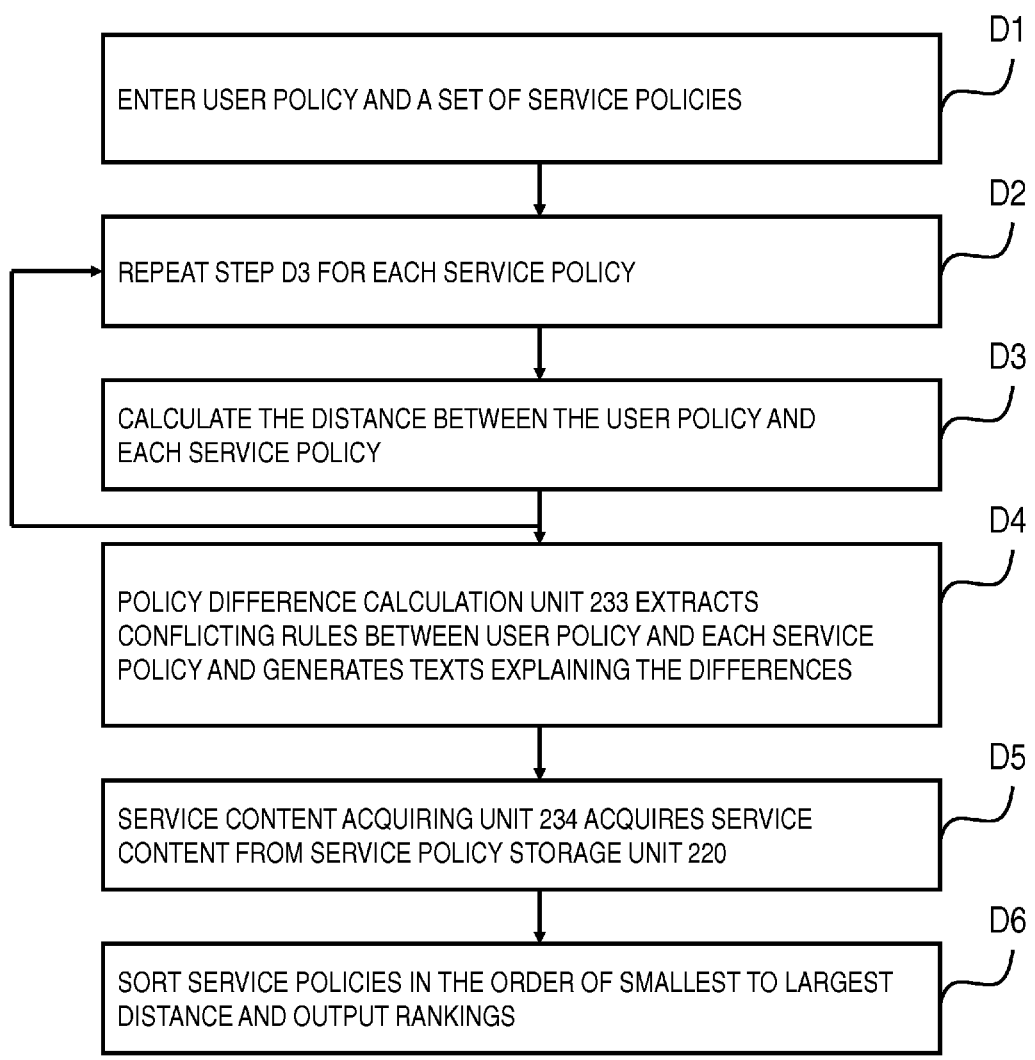
FIG. 18 is a flowchart showing an operation of the ranking generation unit of the arbitration server of the second exemplary embodiment of the present invention.

Next, with reference to a flowchart shown in FIG. 18, an operation of the ranking generation unit 230A of the present exemplary embodiment will be described in detail.

First, a user policy and a set of service policies are entered into the ranking generation unit 230A (step D1). Here, the user policy shown in FIG. 6 and the set of service policies shown in FIG. 17 are assumed to be entered.

Next, the ranking generation unit 230A repeats step D3 for each service policy (step D2). More concretely, the distance between the user policy and each service policy is calculated as in the first exemplary embodiment (the step D3). In the present exemplary embodiment, the calculation results shown in FIG. 12 are assumed to be obtained as in the first exemplary embodiment.

Next, the policy difference calculation unit 233 extracts conflicting rules between the user policy and each service policy and generates texts explaining the differences (step D4). For instance, in a case of the service policy having the service policy ID "4," the rule of the data type "Position" is in conflict, and for example, a text saying, "Must provide the information "Position" that you do not want to provide" is generated as the explanation text.

Next, the service content acquiring unit 234 acquires the service content from the service policy storage unit 220 (step D5). For instance, in the case of the service policy having the service policy ID "4," the service content acquiring unit 234 acquires "Provide recommendations based on location information" as the service content of the service policy.

Finally, the ranking calculation unit 231A sorts the service policies in the order of smallest to largest distance, generates rankings with the texts explaining the differences and the service content added, and transmits the rankings to the privacy information holder terminal 100 (step D6).

FIG. 19 is an example of the service policy rankings sorted and created by the ranking calculation unit 231A of the present exemplary embodiment. As shown in FIG. 12, the service policy having the service policy ID "5" is displayed at the top since it has the smallest distance (d=0) to the user policy. Further, the policy difference information is "NONE" because the service policy having the service policy ID "5" does not have any difference. Meanwhile, each of the other service policies has a difference; therefore, the content of the differences are displayed as the policy difference information.

Figure 20:
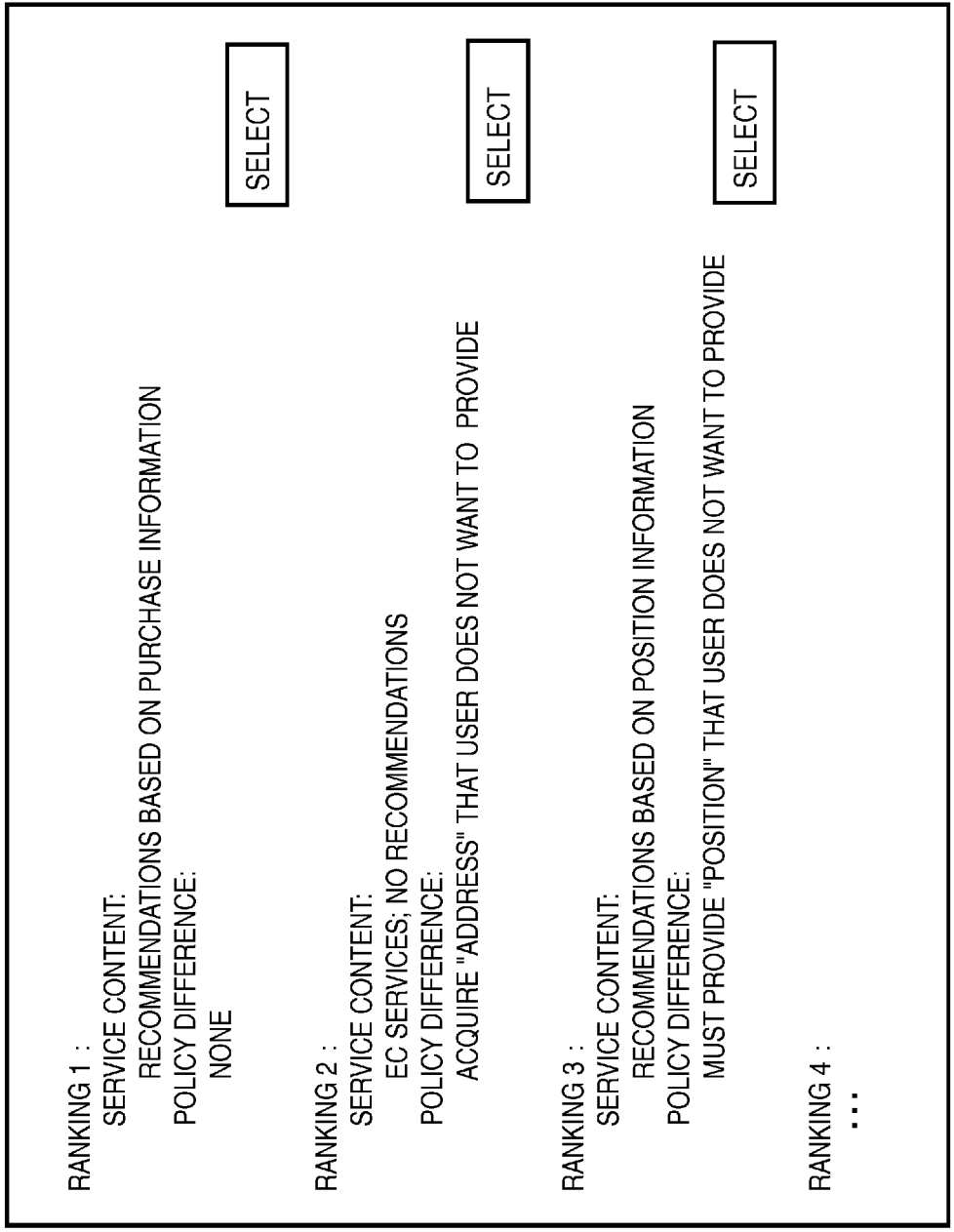
FIG. 20 is an example of a service policy ranking display screen displayed by a ranking display unit of the arbitration server of the second exemplary embodiment of the present invention.

Next, the ranking display unit 120 receives and displays the service policy rankings. FIG. 20 is an example of the service policy rankings displayed by the ranking display unit 120 of the privacy information holder terminal 100 using the service policy rankings shown in FIG. 19.

As described, in the present exemplary embodiment, it is possible to present the privacy information holder with the policy difference that explains conflicting rules between the user policy and each service policy, and the content of the service that the privacy information holder is able to receive when he agrees to each service policy, in addition to the user policy and the service policy rankings.

As a result, in the present exemplary embodiment, it becomes possible to encourage the privacy information holder to select a service policy in which a difference is recognized as an agreed policy by considering the service content thereof and the privacy information utilized, in addition to the effects of the first exemplary embodiment.

Third Exemplary Embodiment

Next, a third exemplary embodiment of the present invention, in which the configuration of the policy distance calculation unit 232 of the first exemplary embodiment is changed so as to enable more detailed calculation of the distance between the policies and more flexible policy arbitration, will be described in detail with reference to the drawings. The differences from the first exemplary embodiment will be mainly explained below.

Figure 21:
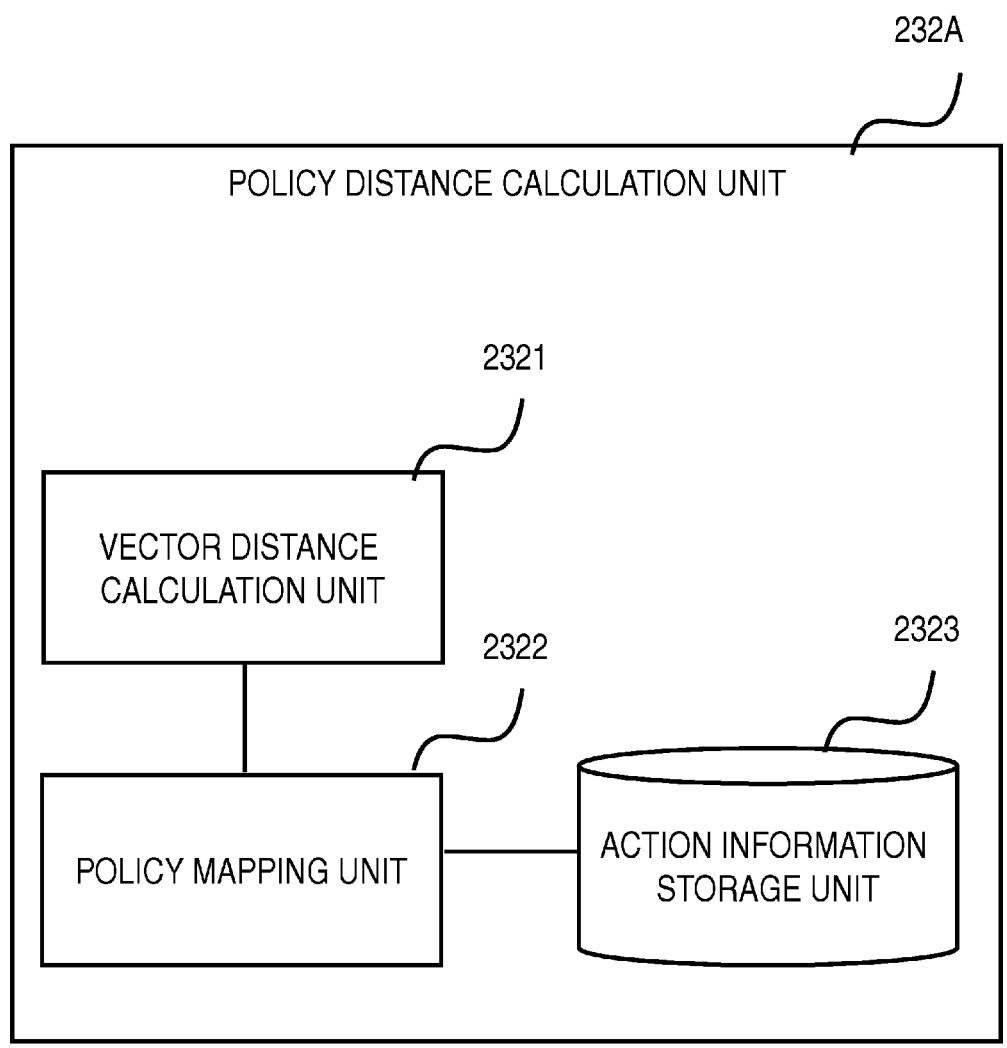
FIG. 21 is a block diagram showing a detailed configuration of a policy distance calculation unit of an arbitration server of a third exemplary embodiment of the present invention.

FIG. 21 is a block diagram showing a configuration of a policy distance calculation unit 232A in the ranking generation unit of an arbitration server of the third exemplary embodiment of the present invention. With reference to FIG. 21, the configuration comprises a policy mapping unit 2322 for mapping the action of each data type written in user and service policies to a protection vector, which is a real value or real-valued vector, an action information storage unit 2323 for storing the relation between the action and the real-valued vector, and a vector distance calculation unit 2321 for calculating the distance between vectors using the protection vector. Here, the protection vector is a real value or real-valued vector indicating the level of privacy protection derived from the action, which is the content of a rule.

In the present exemplary embodiment, as shown in FIG. 22, as actions (how to handle privacy information, i.e., the content of a rule), not only the binary values ("Provide," "Do not provide," "Acquire," "Do not acquire"), but also an action "Protect" can be handled. Here, the action "Protect" indicates that processing of privacy protection will be provided. In the present exemplary embodiment, since the distance is not the simple calculation of the total number of conflicting rules as in the first and the second exemplary embodiments, an increase in the description capability of the policies can be supported.

Further, in the description of the present exemplary embodiment, the service policy storage unit 220 is assumed to store service policies in which service policy IDs and the action "Protect" are set, as shown in FIG. 23.

Next, an operation of the present exemplary embodiment will be described in detail with reference to the drawings. First, a method for calculating the distance between user and service policies of the present exemplary embodiment (corresponding to the step B3 in FIG. 4 of the first exemplary embodiment) will be described. Note that explanations of the other operations are omitted since they are the same as those in the first exemplary embodiment.

Figure 24:
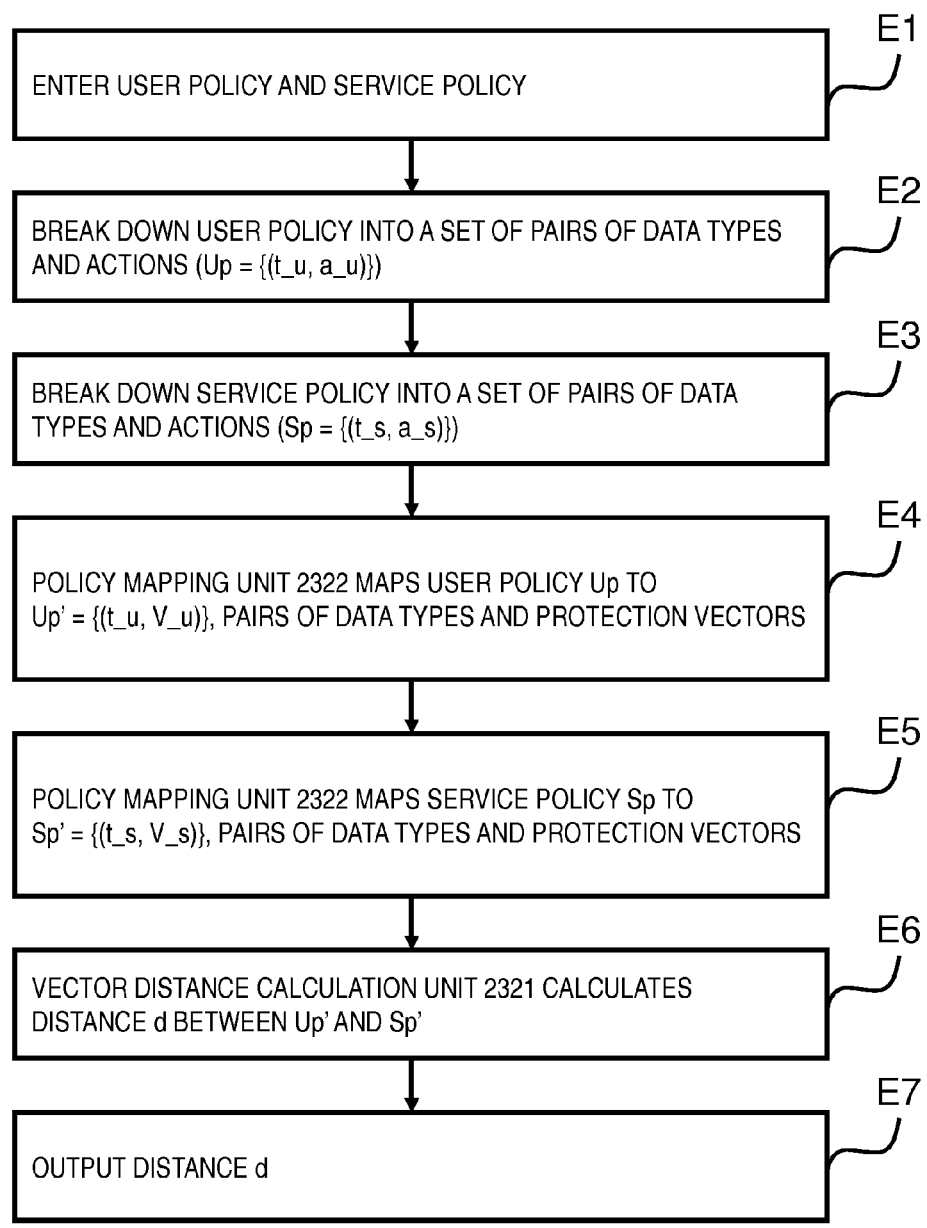
FIG. 24 is a flowchart showing an operation of the policy distance calculation unit of the arbitration server of the third exemplary embodiment of the present invention.

FIG. 24 is a flowchart showing an operation of the policy distance calculation unit 232A of an arbitration server of the third exemplary embodiment of the present invention. With reference to FIG. 24, first a user policy and a service policy are entered into the policy distance calculation unit 232A (step E1). Here, the user policy shown in FIG. 22 and the service policy having the service policy ID "3" shown in FIG. 23 are assumed to be entered.

Next, the policy distance calculation unit 232A breaks down the user policy into a set of pairs of data types and actions (Up={(t_u, a_u)}) (step E2). For instance, the user policy in FIG. 22 is broken down into Up={("NAME," "Provide"), ("Address," "Do not provide"), ("Position," "Protect"), ("Buying," "Provide")}.

Next, the policy distance calculation unit 232A breaks down the service policy into a set of pairs of data types and actions (Sp={(t_s, a_s)}) (step E3). For instance, the service policy having the service policy ID "3" in FIG. 23 is broken down into Sp={("NAME," "Acquire"), ("Address," "Acquire"), ("Position," "Protect"), ("Buying," "Do not acquire")}.

Next, the policy mapping unit 2322 maps the actions to protection vectors by referring to the action information storage unit 2323 and maps the user policy Up to Up'={(t_u, V_u)}, a set of pairs of the data types and the protection vectors (step E4).

Figure 25:
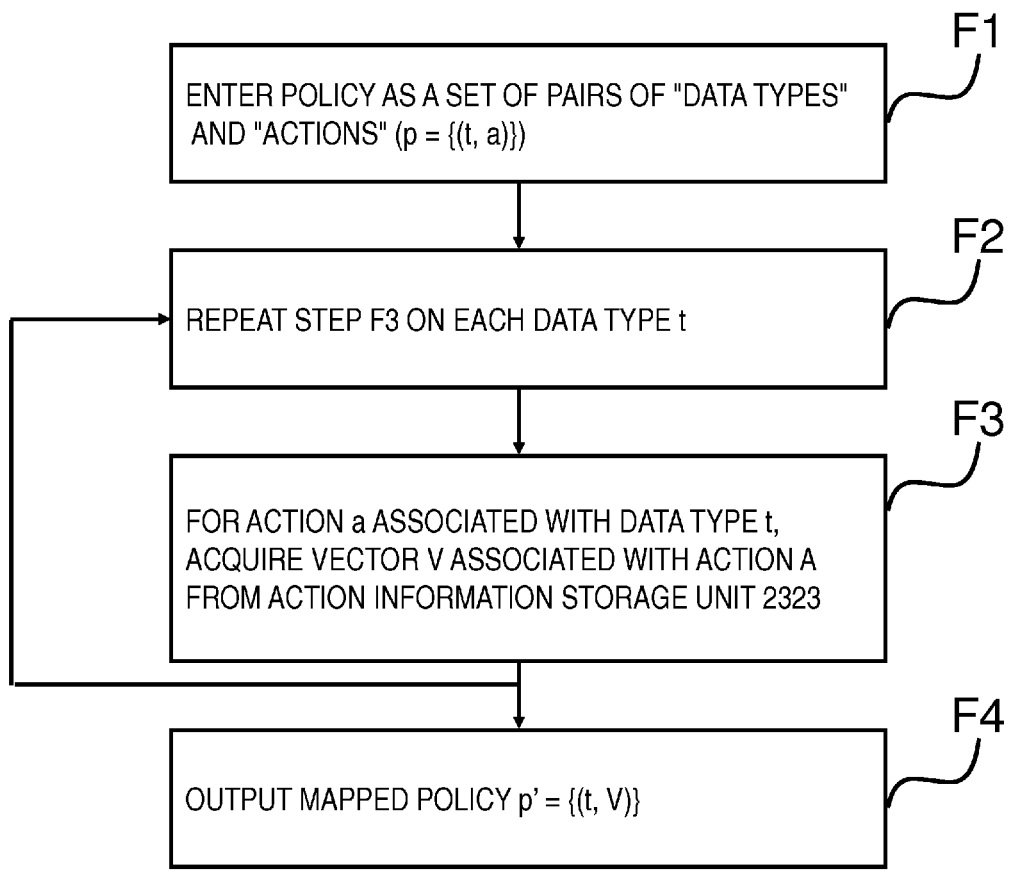
FIG. 25 is a flowchart showing an operation of a policy mapping unit of the arbitration server of the third exemplary embodiment of the present invention.

The procedure of mapping the policy to the protection vectors in the step E4 will be described in detail with reference to FIG. 25.

First, a policy p={(t, a)} is entered into the policy mapping unit 2322. Here, the broken down user policy p={("NAME," "Provide"), ("Address," "Do not provide"), ("Position," "Protect"), ("Buying," "Provide")} is entered.

Next, the policy mapping unit 2322 executes the processing of step F3 on each data type t (step F2).

More concretely, for an action a associated with a data type t, the policy mapping unit 2322 acquires a vector V associated with the action a from the action information storage unit 2323 (the step F3). For instance, when the action information storage unit 2323 defines the associations between the rules and the real-valued vectors in a table shown in FIG. 26, a one-dimensional vector V=(0) is acquired from the action "Provide" of the data type "NAME."

After completing the processing of the step F3 on each data type, the policy mapping unit 2322 outputs a mapped policy p'={(t, V)} (step F4). For instance, when the table shown in FIG. 26 is used, mapped policy vectors p'={("NAME," (0)), ("Address," (1)), ("Position," (0.5)), ("Buying," (0))} are obtained from the user policy shown in FIG. 22.

With reference to FIG. 24 again, the policy mapping unit 2322 refers to the action information storage unit 2323 and maps the service policy Sp to a policy vector Sp'={(t_s, V_s)}, a set of pairs of data types and protection vectors (step E5). By performing mapping as in the case of the user policy, mapped policy vectors p'={("NAME," (0)), ("Address," (0)), ("Position," (0.5)), ("Buying," (1))} are obtained from the service policy having the service policy ID "3: in FIG. 23.

Finally, the service policy in FIG. 23 is mapped as shown in FIG. 27. Next, the vector distance calculation unit 2321 calculates a distance d between the mapped policies Up' and Sp' (step E6).

Figure 28:
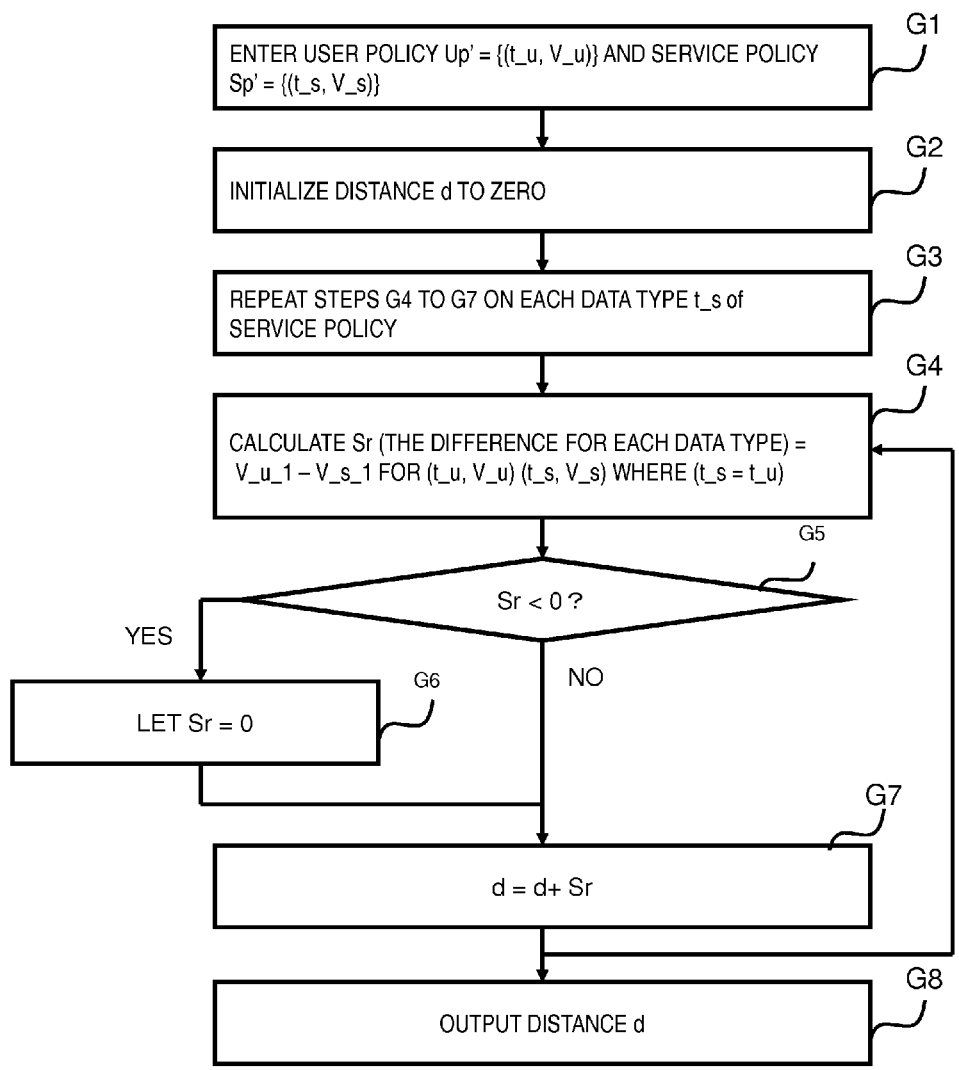
FIG. 28 is a flowchart showing an operation of a vector distance calculation unit of the arbitration server of the third exemplary embodiment of the present invention.

Here, the calculation of the distance between Up' and Sp' in the step E6 will be described with reference to a flowchart in FIG. 28.

First, the user policy vector Up'={(t_u, V_u)} and the service policy vector Sp'={(t_s, V_s)} are entered into the vector distance calculation unit 2321 (step G1).

Next, the vector distance calculation unit 2321 initializes the distance d to zero (step G2). Next, the vector distance calculation unit 2321 executes the processing of steps G4 to G7 on each data type t_s of the service policy (step G3).

More concretely, the vector distance calculation unit 2321 extracts pair combinations (t_u, V_u), (t_s, V_s) in which the data types match (t_s=t_u), and calculates Sr, the difference for each data type, as Sr=V_u_1−V_s_1 (the step G4). Here, V_u_1 denotes a one-dimensional element of V_u. For instance, when t_s="Address," V_u=(1), V_s=(0), and Sr is calculated as Sr=1−0=1.

Next, the vector distance calculation unit 2321 determines whether or not Sr satisfies Sr<0 (the step G5). When Yes, the operation moves to the step G6, and when No, it moves to the step G7. In the case of t_s="Address," the operation moves to the step G7 since Sr=1.

When Yes in the step G5, the vector distance calculation unit 2321 deems Sr to be zero (the step G6).

Next, the vector distance calculation unit 2321 lets d=d+Sr (the step G7).

After completing the steps G4 to G7 on each t_s, the vector distance calculation unit 2321 outputs the distance d (step G8). From the sum of the differences between the mapped policy p'={("NAME," (0)), ("Address," (1)), ("Position," (0.5)), ("Buying," (0))} derived from the user policy in FIG. 22 and p'={("NAME," (0)), ("Address," (0)), ("Position," (0.5)), ("Buying," (1))} in the case of the service policy having the service policy ID "3" in FIG. 23, d=1 is outputted.

FIG. 29 is a drawing showing the results of calculating the distances between the user policy in FIG. 22 and all the service policies in FIG. 23.

The ranking generation unit of the present exemplary embodiment generates service policy rankings using the distances calculated as described.

As described, according to the present exemplary embodiment, policy arbitration can be performed for various policy formats. The reason is that the policy mapping unit 2322 maps policies to real-valued vectors based on the information stored in the action information storage unit 2323, and using these vectors, the vector distance calculation unit 2321 calculates the distance between the policies by calculating the distances between the vectors.

Further, in the exemplary embodiment described above, the protection vectors are derived from the actions, regardless of the data type, using the table shown in FIG. 26, however, it is possible to define the value of a protection vector corresponding to an action for each data type. In this way, the distance can be calculated to be large for a conflict regarding sensitive privacy information.

It should be noted that other objects, features and aspects of the present invention will become apparent in the entire disclosure and that modifications may be done without departing the gist and scope of the present invention as disclosed herein and claimed as appended herewith.

Also it should be noted that any combination of the disclosed and/or claimed elements, matters and/or items may fall under the modifications aforementioned.

For instance, the data types of the user policies and the service policies cited in the descriptions of the exemplary embodiments are merely examples, and they can be suitably changed according to the privacy information to which the present invention is applied.

Further, the flowcharts used to describe the exemplary embodiment above are shown in simplified forms to facilitate understanding of the present invention and it is possible to add various modifications thereto.

Finally, preferred modes of the present invention are summarized.

(Mode 1)

Refer to the policy arbitration method according to the first aspect.

(Mode 2)

The policy arbitration method according to Mode 1, wherein the service policy ranking is obtained by sorting the service policy set in an order of smallest to largest degree of divergence between the user policy and the service policy.

(Mode 3)

The policy arbitration method according to Mode 1 or 2, wherein a number of conflicting rules between the user policy and the service policy is used to calculate the degree of divergence between the user policy and the service policy.

(Mode 4)

The policy arbitration method according to any one of Modes 1 to 3, wherein
calculating the degree of divergence between the user policy and the service policy comprises:
mapping the user policy to a user policy vector by converting the rule into a real value or real-valued vector;
mapping the service policy to a service policy vector by converting the rule into a real value or real-valued vector; and
calculating the degree of divergence using the user policy vector and the service policy vector.

(Mode 5)

The policy arbitration method according to any one of Modes 1 to 4, further comprising:
extracting a difference between the user policy and the service policy; and
displaying the difference as information accompanying the service policy ranking.

(Mode 6)

The policy arbitration method according to any one of Modes 1 to 5, further comprising:
extracting a characteristic of the service policy; and
displaying the characteristic of the service policy as information accompanying the service policy ranking.

(Mode 7)

Refer to the arbitration server according to the second aspect.

(Mode 8)

The arbitration server according to Mode 7, wherein the ranking generation unit generates a ranking in which the service policy set is sorted in an order of smallest to largest degree of divergence between the user policy and the service policy.

(Mode 9)

The arbitration server according to Mode 7 or 8, wherein the ranking generation unit comprises a policy distance calculation unit that calculates the degree of divergence between the user policy and the service policy, by using a number of conflicting rules between the user policy and the service policy.

(Mode 10)

The arbitration server according to any one of Modes 7 to 9, wherein the ranking generation unit comprises:
a policy mapping unit that maps the user policy and the service policy to a user policy vector and service policy vector, respectively, by converting the rule into a real value or real-valued vector; and
a vector distance calculation unit that calculates the degree of divergence using the user policy vector and the service policy vector.

(Mode 11)

The arbitration server according to any one of Modes 7 to 10, further comprising an action information storage unit that stores a table that defines a real value or real-valued vector corresponding to content of the rule, wherein
the rule is converted into a real value or real-valued vector by referring to the table.

(Mode 12)

The arbitration server according to any one of Modes 7 to 11, wherein the table of the action information storage unit defines a real value or real-valued vector corresponding to content of the rule for each data type.

(Mode 13)

The arbitration server according to any one of Modes 7 to 12, further comprising a policy difference calculation unit that extracts a difference between the user policy and the service policy, wherein the difference is displayed as information accompanying the service policy ranking.

(Mode 14)

The arbitration server according to any one of Modes 7 to 13, further comprising a service content acquiring unit that extracts a characteristic of the service policy, wherein the characteristic of the service policy is displayed as information accompanying the service policy ranking.

(Mode 15)

Refer to the program according to the third aspect.

The entire disclosures of the above Patent Literatures and Non-Patent Literatures are incorporated herein by reference thereto. Modifications and adjustments of the exemplary embodiment are possible within the scope of the overall disclosure (including the claims) of the present invention and based on the basic technical concept of the present invention. Various combinations and selections of various disclosed elements (including each element of each claim, each element of each exemplary embodiment, each element of each drawing, etc.) are possible within the scope of the claims of the present invention. That is, the present invention of course includes various variations and modifications that could be made by those skilled in the art according to the overall disclosure including the claims and the technical concept. Particularly, any numerical range disclosed herein should be interpreted that any intermediate values or subranges falling within the disclosed range are also concretely disclosed even without specific recital thereof.

The present invention can be applied to uses such as a recommendation service utilizing privacy information and privacy policy arbitration in an SNS (Social Networking Service).

100: privacy information holder terminal
110: user policy input unit
120: ranking display unit
130: agreed policy selection unit
200: arbitration server
210: user policy receiving unit
220: service policy storage unit
230, 230A: ranking generation unit
231, 231A: ranking calculation unit
232, 232A: policy distance calculation unit
233: policy difference calculation unit
234: service content acquiring unit
2321: vector distance calculation unit
2322: policy mapping unit
2323: action information storage unit
240: agreed policy receiving unit
250: agreed policy storage unit

What is claimed is:

1. An arbitration server, comprising:
a user policy receiving unit configured to receive from a user a user policy, the user policy describing at least one rule pairing a data type of privacy information possessed by the user and privacy requirements of the user for the data type;
a ranking generation unit configured to generate a ranking of at least one service policy of a service policy set based on a degree of divergence between the user policy and the at least one service policy, the at least one service policy describing at least one rule that is a pair of a data type of privacy information and access requirements of the data type of a service;
a ranking display unit configured to display the service policy ranking;
an agreed policy receiving unit configured to receive a selection of a service policy from the displayed service policy ranking; and
an agreed policy storage unit configured to store the selected service policy and apply the selected service policy to the privacy information of the user,
wherein the ranking generation unit comprises:
a policy mapping unit configured to map the user policy and the at least one service policy to a user policy vector and service policy vector, respectively, by converting the respective at least one rule into a real value or real-valued vector; and
a vector distance calculation unit configured to calculate the degree of divergence using the user policy vector and the service policy vector.

2. The arbitration server according to claim 1, wherein the ranking generation unit is further configured to generate the ranking in which the service policy set is sorted in an order of smallest to largest degree of divergence between the user policy and the at least one service policy.

3. The arbitration server according to claim 1, wherein the ranking generation unit further comprises a policy distance calculation unit configured to calculate the degree of divergence between the user policy and the at least one service policy, by using a number of conflicting rules between the user policy and the at least one service policy.

4. A non-transitory computer-readable recording medium, storing a program that causes a computer to execute:
receiving from a user a user policy, the user policy describing at least one rule pairing a data type of privacy information possessed by the user and privacy requirements of the user for the data type; and
generating a ranking of at least one service policy of a service policy set based on a degree of divergence between the user policy and the at least one service policy, the at least one service policy describing at least one rule that is a pair of a data type of privacy information and access requirements of the data type of a service; and
calculating the degree of divergence between the user policy and the at least one service policy by:
mapping the user policy to a user policy vector by converting the at least one rule of the user policy into a real value or real-valued vector;
mapping the at least one service policy to a service policy vector by converting the at least one rule of the at least one service policy into a real value or real-valued vector; and
calculating the degree of divergence using the user policy vector and the service policy vector;
displaying the service policy ranking;
receiving a selection of a service policy from the displayed service policy ranking;
storing the selected service policy; and
applying the selected service policy to the privacy information of the user.

5. The non-transitory computer-readable recording medium according to claim 4, wherein the service policy ranking is obtained by sorting the service policy set in an order of smallest to largest degree of divergence between the user policy and the at least one service policy.

6. The non-transitory computer-readable recording medium according to claim 4, wherein a number of conflicting rules between the user policy and the at least one service policy is used to calculate the degree of divergence between the user policy and the at least one service policy.

7. The non-transitory computer-readable recording medium according to claim 4, wherein the program further causes the computer to execute:
   extracting a difference between the user policy and the at least one service policy; and
   displaying the difference as information accompanying the service policy ranking.

8. The non-transitory computer-readable recording medium according to claim 4, wherein the program further causes the computer to execute:
   extracting a characteristic of the at least one service policy; and
   displaying the characteristic of the at least one service policy as information accompanying the service policy ranking.

9. A policy arbitration method, comprising:
   entering a user policy in which a privacy information holder describes at least one rule pairing a data type of privacy information possessed by the privacy information holder and privacy requirements of the privacy information holder for the data type;
   generating a ranking of at least one service policy of a service policy set based on a degree of divergence between the user policy and the at least one service policy, the at least one service policy describing at least one rule that is a pair of a data type of privacy information and access requirements of the data type of a service;
   mapping the user policy to a user policy vector by converting the at least one rule of the user policy into a real value or real-valued vector;
   mapping the at least one service policy to a service policy vector by converting the at least one rule of the at least one service policy into a real value or real-valued vector; and
   calculating the degree of divergence using the user policy vector and the at least one service policy vector;
   displaying the service policy ranking on a privacy information holder terminal;
   receiving, from the privacy information holder terminal, a selection of a service policy from the displayed service policy ranking;
   storing the selected service policy; and
   applying the selected service policy to the privacy information of the privacy information holder.

10. The policy arbitration method according to claim 9, wherein the service policy ranking is obtained by sorting the service policy set in an order of smallest to largest degree of divergence between the user policy and the at least one service policy.

11. The policy arbitration method according to claim 9, wherein a number of conflicting rules between the user policy and the at least one service policy is used to calculate the degree of divergence between the user policy and the at least one service policy.

12. The policy arbitration method according to claim 9, further comprising:
   extracting a difference between the user policy and the at least one service policy; and
   displaying the difference as information accompanying the service policy ranking.

13. The policy arbitration method according to claim 9, further comprising:
   extracting a characteristic of the at least one service policy; and
   displaying the characteristic of the at least one service policy as information accompanying the service policy ranking.

14. The policy arbitration method according to claim 9, wherein the receiving comprises having the privacy information holder select one service policy from the displayed service policy ranking.

* * * * *